United States Patent [19]
Perrier et al.

[11] Patent Number: 6,020,339
[45] Date of Patent: Feb. 1, 2000

[54] ARYL FURAN DERIVATIVES AS PDE IV INHIBITORS

[75] Inventors: Helene Perrier; Yongxin Han; Christopher Bayly; Dwight Mac Donald; Andre Giroux; Robert N. Young, all of Quebec, Canada

[73] Assignee: Merck & Co., Inc., Rahway, N.J.

[21] Appl. No.: 09/163,032

[22] Filed: Sep. 28, 1998

Related U.S. Application Data

[60] Provisional application No. 60/061,261, Oct. 3, 1997.

[51] Int. Cl.[7] .................. A61K 31/505; A61K 31/34; C07D 401/00; C07D 277/62
[52] U.S. Cl. .................. 514/269; 514/262; 514/336; 514/367; 514/375; 514/397; 514/461; 544/265; 546/283.4; 548/170; 548/222; 548/315.7; 549/497; 549/499; 549/502
[58] Field of Search .................. 549/501, 497, 549/499, 502; 514/461, 269, 262, 336, 367, 375, 397; 544/300, 265; 546/283.4; 548/170, 222, 315.7

[56] References Cited

U.S. PATENT DOCUMENTS

| | | | |
|---|---|---|---|
| 2,641,601 | 6/1953 | Goldberg et al. | |
| 3,222,290 | 12/1965 | Braus et al. | 549/501 |
| 3,531,497 | 9/1970 | Youngdale | |
| 3,557,005 | 1/1971 | Broaddus | |
| 3,743,656 | 7/1973 | Brown et al. | 549/501 |
| 4,595,693 | 6/1986 | Biftu et al. | |
| 4,927,851 | 5/1990 | Damon, II et al. | 514/460 |
| 5,474,995 | 12/1995 | Durcharme et al. | 514/241 |
| 5,602,172 | 2/1997 | Boykin et al. | 514/461 |
| 5,629,340 | 5/1997 | Kuwano et al. | 514/461 |

FOREIGN PATENT DOCUMENTS

| | | |
|---|---|---|
| 0 318 066 A1 | 5/1989 | European Pat. Off. |
| 58-0036298 | 3/1983 | Japan |
| 02180846 | 7/1990 | Japan |
| 7-0157634 | 6/1995 | Japan |
| 8-0008276 | 1/1996 | Japan |
| 0 678 296 A1 | 10/1995 | WIPO |
| 96JP01458 | 5/1996 | WIPO |
| WO96JP01636 | 6/1996 | WIPO |

OTHER PUBLICATIONS

Pouzet, P. et al. J. Chem. Soc. Chem. Commun. 1995 pp. 473–474.
Burger, K. et al. J. prakt. Chem. 334: 311–316 (1992).
Takahashi, K. et al. Bull. Chem. Soc. Jpn. 65: 1855–1859 (1992).
Rio, G. et al. Bull. Soc. Chim. France 12: 2824–2832 (1974.
Lutz, R.E. et al. J. Am. Chem. Soc. 64: 2583–2585 (1942).
Yates, P. et al. J. Am. Chem. Soc. 80: 196–201 (1958).
Hall, J.H. et al. J. Heterocycl. Chem. 29(5): 1245–1273 (1992).
Bailey, P.S. et al. J. Org. Chem. 21:297–302 (1956).
Watanabe, M. et al. Chem. Pharm. Bull. 37(11):2914–2919 (1989).
Das, B. P. et al. J. Med. Chem. 20(4):531–536 (1977).
Auterhoff, H. et al. Arch. Pharm. 299(7) 618–626 (1966). and Abstract.
Gump, K. et al. J. Am. Chem. Soc. 89(25): 6770–6771 (1967) with abstract.
Kumar, A. et al. Synth. Commun. 25(14): 2071–2078 (1995) with abstract.
Iyer, R. N. et al. Indian J. Chem. 11(12): 1260–1262 (1973) with abstract.
Traverso, V. G. Gass. Chil. Ital. 89: 1810–1817 (1959) with abstract.

*Primary Examiner*—Deborah C. Lambkin
*Attorney, Agent, or Firm*—Shu M. Lee; David L. Rose

[57] ABSTRACT

The invention encompasses the novel compound of Formula I useful in the treatment of diseases, including asthma, by raising the level of cyclic adenosine-3',5'-monophosphate (cAMP) through the inhibition of phosphodiesterase IV (PDE IV).

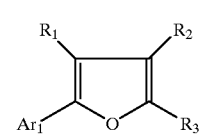

I

The invention also encompasses certain pharmaceutical compositions and methods for treatment of diseases by inhibition of PDE IV, resulting in an elevation of cAMP, comprising the use of compounds of Formula I.

9 Claims, No Drawings

ARYL FURAN DERIVATIVES AS PDE IV INHIBITORS

CROSS REFERENCE TO RELATED APPLICATIONS

This application is a non-provisional application related to U.S. application Ser. No. 60/061,261, filed on Oct. 3, 1997 priority of which is claimed hereunder.

BACKGROUND OF THE INVENTION

This invention relates to compounds and pharmaceutical compositions for the treatment of diseases by raising the level of cyclic adenosine-3',5'-monophosphate (cAMP) through the inhibition of phosphodiesterase IV (PDE IV).

Many hormones and neurotransmitters modulate tissue function by elevating intra-cellular levels of 3',5'-cyclic adenosine monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) *J. Immunol.* 148 2503–2510) and eosinophils (Dent G. et al., (1991) *Br. J. Pharmacol.* 103 1339–1346) and that inhibition of this isotype is associated with the inhibition of cell activation. Furthermore, elevation of cAMP in airway smooth muscle has a spasmolytic effect. Consequently PDE IV inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. For PDE IV, it is has been shown that there are four isoforms (A, B, C and D) each coded for by a separate gene in both rodents (Swinnen J. V. et al., (1989) *Proc. Natl. Acad. Sci. USA* 86 5325–5329) and man (Bolger G. et al., (1993) *Mol. Cell Biol.* 13 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al., 1989; Bolger et al., 1993; Obernolte R. et al., (1993) *Gene* 129 239–247, ibid) and the high degree of sequence conservation amongst isoforms of different species.

To date full length cDNAs for human PDE IVA, B and D (Bolger et al., 1993 ibid; Obernolte et al., 1993 ibid; Mclaughlin M. et al., (1993) *J. Biol. Chem.* 268 6470–6476) and rat PDE IVA, B and D (Davis R. et al., (1989) *Proc. Natl. Acad. Sci. USA* 86 3604–3608; Swinnen J. V. et al., (1991) *J. Biol. Chem.* 266 18370–18377), have been reported, enabling functional recombinant enzymes to be produced by expression of the cDNAs in an appropriate host cell. These cDNAs have been isolated by conventional hybridisation methods. However using this approach, only partial cDNAs for both human and rat PDE IVC have been obtained. (Bolger et al., ibid. 1993 and Swinnen et al., ibid. 1989 and International Patent Specification No. WO 91/16457.)

The design of PDE IV inhibitors for the treatment of inflammatory diseases such as asthma, has met with limited success to date. Many of the PDE IV inhibitors which have been synthesised have lacked potency and/or inhibit more than one type of PDE isoenzyme in a non-selective manner. PDE IV inhibitors that are relatively potent and selective for PDE IV, are reported to be emetic as well. Indeed this side effect has been so universal that experts have expressed their belief that the emesis experienced upon administration of a PDE IV inhibitor, may be mechanism based.

We have now found a novel series of aryl furan derivatives, members of which compared to known structurally similar compounds are potent inhibitors of PDE IV at concentrations at which they have little or no inhibitory action on other PDE isoenzymes. These compounds inhibit the human recombinant PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. Advantageously, compounds according to the invention have good oral activity and at orally effective doses exhibit little or none of the side-effects associated with known PDE IV inhibitors, such as rolipram. The compounds of the invention are therefore of use in medicine, especially in the prophylaxis and treatment of asthma and other inflammatory conditions.

SUMMARY OF THE INVENTION

The invention encompasses novel compounds of Formula I useful in the treatment of disease by inhibition of PDE IV, resulting in an elevation of cAMP.

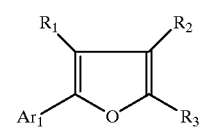

The invention also encompasses certain pharmaceutical compositions and methods for treatment of diseases by inhibition of PDE IV, resulting in an elevation of cAMP, comprising the use of compounds of Formula I.

DETAILED DESCRIPTION OF THE INVENTION

The invention encompasses the novel compound of Formula I useful in the treatment of disease by inhibition of PDE IV, resulting in an elevation of cAMP,

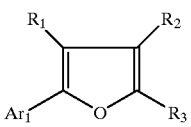

or a pharmaceutically acceptable salt thereof wherein:
$Ar^1$ is an aromatic ring selected from phenyl, pyridinyl or furyl, optionally substituted with up to two substituents selected independently from among:
  a) $C_{1-6}$alkyl, optionally substituted with —OH, —$CO_2H$, $CO_2C_{1-3}$alkyl, and CN,
  b) $C_{1-6}$alkoxy,
  c) $C_{1-3}$alkylthio,
  d) $C_{1-3}$alkylsulfonyl,
  e) $C_{1-3}$fluoroalkyl, optionally substituted with —OH,
  f) halo,
  g) —OH,
  h) —$CO_2H$,
  i) —$CO_2C_{1-3}$alkyl,
$R^1$ is selected from:
  a) hydrogen,
  b) halo,
  c) $C_1$–$C_5$alkylcarbonyloxy,
  d) $C_{1-3}$alkyl, optionally substituted with —OH, N—$C_{1-4}$alkyl, cyclo-N-$C_{5-7}$ alkyl, piperazine, $C_{1-4}$alkylcarbonylpiperazine, morpholine or hydroxypiperidine,
  e) $C_{1-4}$alkylcarbonyl,
  f) tri($C_{1-3}$alkyl)silyl,
  g) N-morpholinyl or
  h) —X—Y—$Ar^2$,
    wherein:
    X is 1) —$CH_2$—,
       2) —CO—, or
       3) a bond;
    Y is 1) —O—,
       2) —S—,
       3) —$S(O)_2$—
       4) —$NR^4$—, or
       5) a bond;
    $Ar^2$ is an aromatic ring selected from phenyl, benzothiazolyl, benzoxazolyl, pyrimidinyl, pyridinyl, purinyl or imidazolyl optionally substituted with up to two substituents selected independently among:
      1) $C_{1-6}$alkyl,
      2) $C_{1-6}$alkoxy,
      3) —OH,
      4) halo, or
      5) $CF_3$;
$R^2$ is selected from:
  a) hydrogen or
  b) $C_{1-3}$alkyl.
$R^3$ is selected from phenyl, pyridinyl, quinolinyl or furyl, optionally substituted with up to two substituents chosen independently among:
  a) $C_{1-3}$alkyl,
  b) $C_{1-3}$fluoroalkyl,
  c) $C_{1-6}$alkoxy,
  d) $C_{1-3}$fluoroalkoxy,
  e) $C_{1-3}$alkylthio,
  f) halo, or
  g) —OH, and
$R^4$ is chosen from among:
  a) hydrogen, or
  b) $C_{1-5}$alkyl.

Within this embodiment there is a preferred genus of compounds wherein
$R^2$ is hydrogen;
and all other variables are defined as in Formula I above.
Another preferred genus is that in which —X—Y— is —$CH_2$—S— and all other variables are as described above.
Another preferred genus is that in which $Ar^2$ is pyrimidinyl, optionally substituted with up to two substituents chosen independently among:
  1) $C_{1-6}$alkyl,
  2) $C_{1-6}$alkoxy,
  3) —OH, or
  4) halo.

Still another preferred genus is realized when: $Ar^1$ is an aromatic ring selected from phenyl, pyridinyl or furyl, optionally substituted with up to two substituents selected independently from among:
  a) $C_{1-6}$alkyl, optionally substituted with —OH, —$CO_2H$, $CO_2C_{1-3}$alkyl, and CN,
  b) $C_{1-6}$alkoxy,
  c) $C_{1-3}$alkylthio,
  d) $C_{1-3}$alkylsulfonyl,
  e) $C_{1-3}$fluoroalkyl, optionally substituted with —OH,
  f) halo,
  g) —OH,
  h) —$CO_2H$,
  i) —$CO_2C_{1-3}$alkyl,
$R^1$ is selected from:
  a) hydrogen,
  b) halo,
  c) $C_{1-3}$ alkyl, optionally substituted with OH,
  h) —X—Y—$Ar^2$,
    wherein:
    X is 1) —$CH_2$—,
       2) —CO—, or
       3) a bond;
    Y is 1) —O—,
       2) —S—,
       3) —$S(O)_2$—
       4) —$NR^4$—, or
       5) a bond;
    $Ar^2$ is an aromatic ring selected from phenyl, pyrimidinyl, pyridinyl, purinyl or imidazolyl optionally substituted with up to two substituents selected independently among:
      1) $C_{1-6}$alkyl,
      2) $C_{1-6}$alkoxy,
      3) —OH,
      4) halo, or
$R^2$ is selected from:
  a) hydrogen or
  b) $C_{1-3}$alkyl.
$R^3$ is selected from phenyl, pyridinyl, or quinolinyl, optionally substituted with up to two substituents chosen independently among:
  a) $C_{1-3}$alkyl,
  b) $C_{1-3}$fluoroalkyl,
  c) $C_{1-6}$alkoxy,
  d) $C_{1-3}$fluoroalkoxy,
  e) $C_{1-3}$alkylthio,
  f) halo, or
  g) —OH, and
$R^4$ is chosen from among:

a) hydrogen, or b) $C_{1-5}$alkyl.

As appreciated by those of skill in the art, halo is intended to include F, Cl, Br, and I.

For purposes of this specification alkyl is defined to include straight, branched, and cyclic structures of the indicated number of carbon atoms. By way of example, $C_{1-6}$alkyl includes methyl, ethyl, propyl, i-propyl, s- and t-butyl, pentyl, hexyl, 1,1-dimethylethyl, cyclopropyl, cyclobutyl, cyclopentyl and cyclohexyl. Similarly, alkoxy, alkylthio, alkylsulfinyl, alkylsulfonyl and alkylcarbonyl mean the corresponding groups of the indicated number of carbon atoms of a straight, branched, or cyclic configuration. Examples of alkoxy groups include methoxy, ethoxy, propoxy, isopropoxy, cyclopropyloxy, cyclohexyloxy, and the like. Examples of alkylthio groups include methylthio, propylthio, isopropylthio, cycloheptylthio, etc. By way of illustration, the propylthio group signifies —$SCH_2CH_2CH_3$. Fluoroalkyl means an alkyl group of the indicated number of carbon atoms, of straight, branched or cyclic structure, in which one or more hydrogen atoms have been replaced by fluorine atoms; fluoroalkoxy, fluoroalkylthio, fluoroalkylsulfinyl, and fluoroalkylsulfonyl have the analogous meanings.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for treatment of disease by inhibition of PDE IV, as disclosed herein comprising a pharmaceutically acceptable carrier and a non-toxic therapeutically effective amount of compound of Formula I as described above.

Within this embodiment the invention encompasses pharmaceutical compositions for treatment of disease by inhibition of PDE IV, resulting in an elevation of cAMP, as disclosed herein comprising a pharmaceutically acceptable carrier and a non-toxic therapeutically effective amount of compound of Formula I as described above.

For purposes of this specification a compound is said to selectively inhibit PDE IV in preference to other PDE's if the ratio of the IC50 concentration for all other PDE inhibition to PDE IV inhibition is 100 or greater.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes, alzheimers disease, allergic rhinitis, allergic conjunctivitis, vernal conjunctivitis, arterial restenosis and atherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, multiple sclerosis, ankylosing spondylitis, transplant rejection and graft versus host disease.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteo-arthritis.

Over-production of cytokines such as TNF in bacterial, fungal or viral infections or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of Formula I together with one or more pharmaceutically acceptable carriers, excipients or diluents.

For the treatment of any of these, compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols; for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Exemplifying the invention are:

EXAMPLE 1

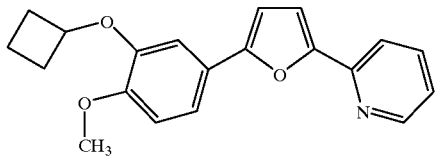

Proton NMR (300 MHz, acetone-d6): 8.55 (d, 1H), 7.85 (dd, 2H), 7.42 (dd, 1H), 7.28 (d, 1H), 7.22 (m, 1H), 7.13 (d, 1H), 7.05 (d, 1H), 6.85 (d, 1H), 4.80 (m, 1H), 3.85 (s, 3H), 2.51 (m, 2H), 2.18 (m, 2H), 1.85 (q, 1H), 1.70 (q, 1H).

EXAMPLE 2

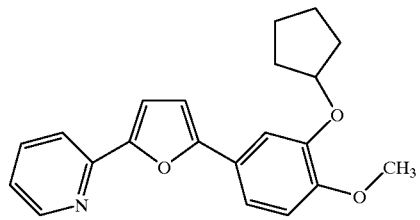

Proton NMR (300 MHz, acetone-d6): 8.53 (d, 1H), 7.84 (m, 2H), 7.42 (m, 2H), 7.23 (m, 1H), 7.17 (d, 1H), 7.03 (d, 1H), 6.96 (d, 1H), 4.95 (m, 1H), 3.84 (s, 3H), 1.98–1.78 (m, 6H), 1.65 (m, 2H).

EXAMPLE 3

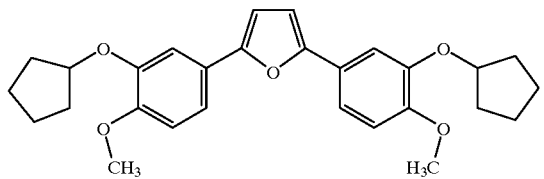

Proton NMR (300 MHz, acetone-d6): 7.48 (s, 1H), 7.45 (d, 1H), 7.0 (d, 1H), 6.75 (s, 1H), 4.95 (m, 1H), 3.8 (s, 3H), 1.98–1.75 (m, 6H), 1.65 (m, 2H).

EXAMPLE 4

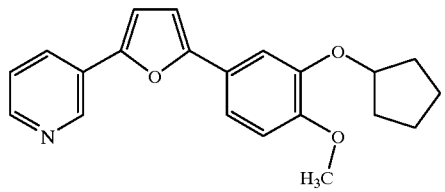

Proton NMR (300 MHz, acetone-d6): 9.05 (s, 1H), 8.48 (dd, 1H), 8.1 (dd, 1H), 7.4 (m, 3H), 7.05(dd, 1H), 7.05(dd, 1H), 7.00 (dd, 1H), 6.85 (dd, 1H), 4.95 (m, 1H), 3.80 (s, 3H), 1.98–1.75 (m, 6H), 1.60(m, 2H).

EXAMPLE 5

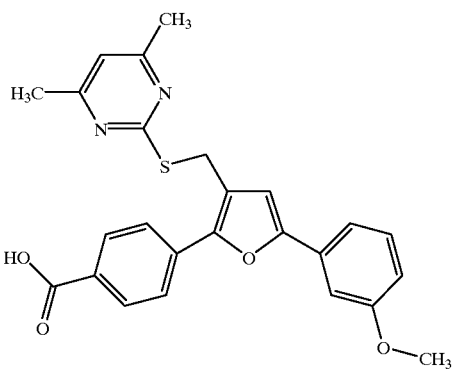

Proton NMR (400 MHz, acetone-d6): 8.16 (d, 2H), 8.00 (d, 2H), 7.40–7.30 (m, 3H), 7.10 (s, 1H), 6.90 (m, 2H), 4.59 (s, 2H), 3.88 (s, 3H), 2.30 (s, 6H).

EXAMPLE 6
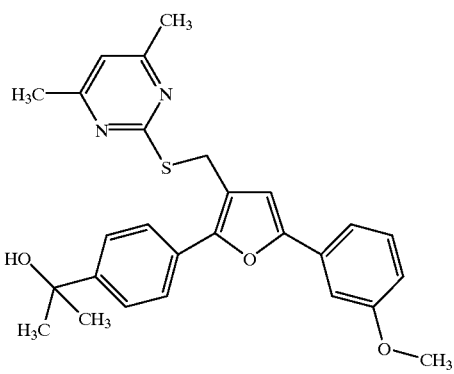
Proton NMR (400 MHz, acetone-d6): 7.80 (d, 2H), 7.65 (d, 2H), 7.38–7.28 (m, 3H), 7.06 (s, 1H), 6.89 (s, 1H), 6.88 (m, 1H), 4.53 (s, 2H), 3.87 (s, 3H), 2.35 (s, 6H), 1.56 (s, 6H).
EXAMPLE 7
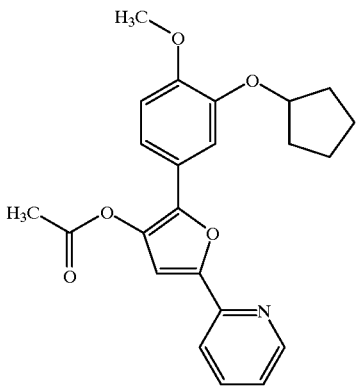
Proton NMR (300 MHz, acetone-d6): 8.58 (d, 1H), 7.7 (bs, 2H), 7.35 (dd, 2H), 7.25 (s, 1H), 7.10 (m, 1H), 6.91 (dd, 1H), 4.82 (m, 1H), 3.88 (s, 3H), 2.3 (s, 3H), 1.98–1.75 (m, 6H), 1.60 (m, 2H).
EXAMPLE 8
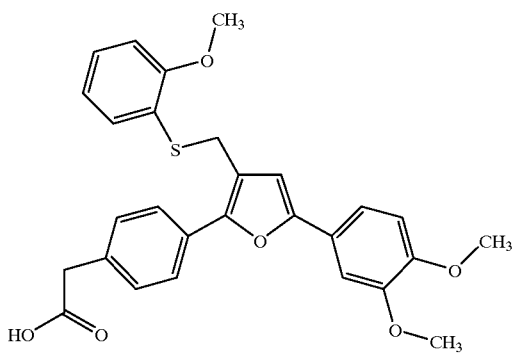
Proton NMR (400 MHz, acetone-d6): 7.73 (d, 2H), 7.41 (d, 2H), 7.39–7.28 (m, 2H), 7.21–7.14 (m, 1H), 7.00–6.87 (m, 3H), 6.86 (s, 1H), 6.75 (d, 1H), 4.33 (s, 2H), 3.89 (s, 2H), 3.83 (s, 3H), 3.69 (s, 3H), 3.68 (s, 3H).
EXAMPLE 9
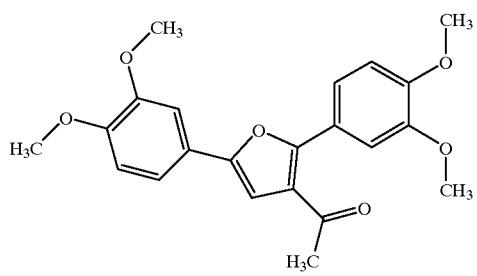
Proton NMR (300 MHz, acetone-d6): 7.78 (s, 1H), 7.55 (dd, 2H), 7.3 (dd, 2H), 7.15 (s, 1H) 6.9 (m, 1H), 3.95 (m, 12H), 2.45 (s, 3H).
EXAMPLE 10
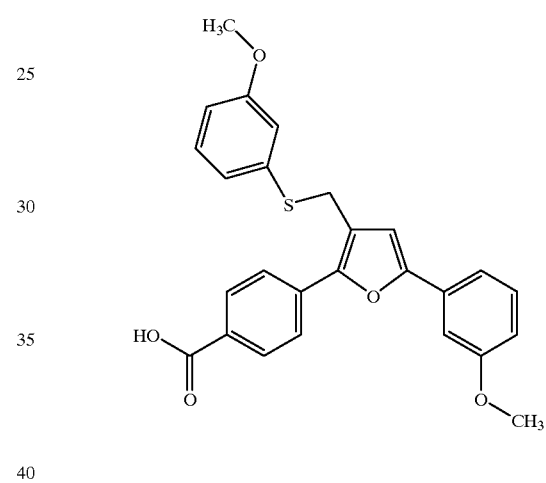
HPLC-MS: 445.3 (M−1).
EXAMPLE 11
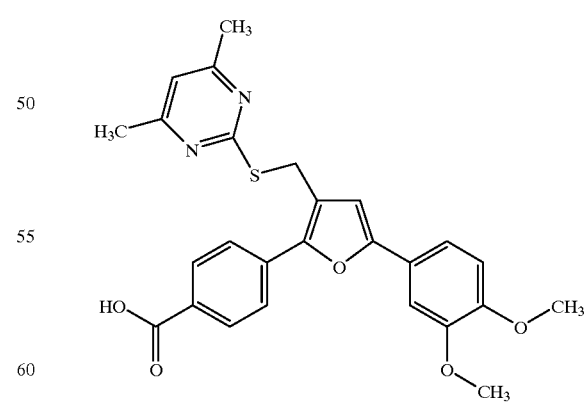
Proton NMR (400 MHz, acetone-d6): 8.14 (d, 2H), 7.98 (d, 2H), 7.38 (m, 2H), 7.03 (d, 1H), 7.00 (s, 1H), 6.90 (s, 1H), 4.58 (s, 2H), 3.89 (s, 3H), 3.84 (s, 3H), 2.32 (s, 6H).

EXAMPLE 12
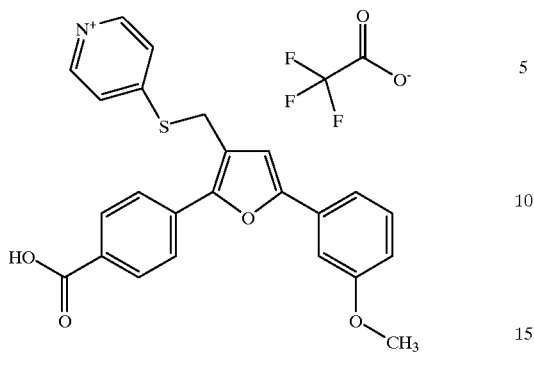
Proton NMR (400 MHz, acetone-d6): 8.70 (d, 1H), 8.14 (d, 2H), 7.99 (d, 2H), 7.84 (d, 2H), 7.45–7.35 (m, 3H), 7.18 (s, 1H), 6.90 (m, 1H), 4.83 (s, 2H), 3.86 (s, 3H).
EXAMPLE 13
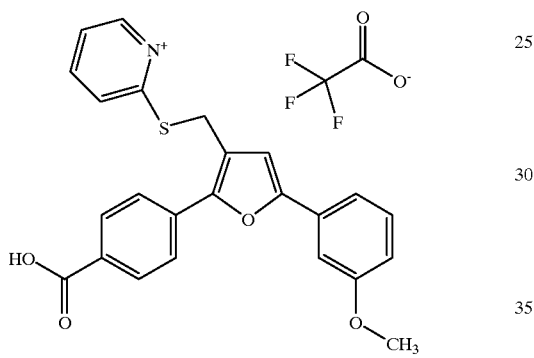
Proton NMR (400 MHz, acetone-d6): 8.45 (dm, 1H), 8.14 (d, 2H), 7.99 (d, 2H), 7.63 (m, 1H), 7.45–7.28 (m, 4H), 7.12 (m, 1H), 7.10 (s, 1H), 6.90 (m, 1H), 4.63 (s, 2H), 3.86 (s, 3H).
EXAMPLE 14
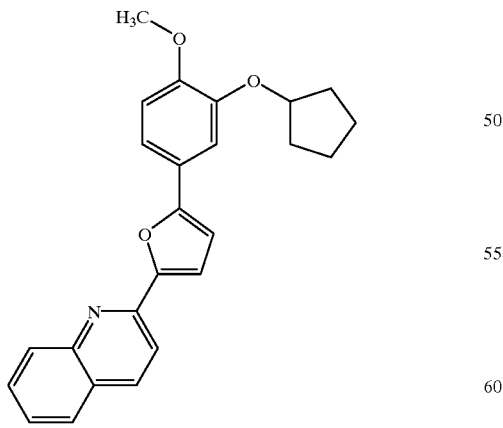
Proton NMR (300 MHz, acetone-d6): 8.38 (d, 1H), 8.1 (d, 1H), 8.05 (d, 1H) 7.95 (d, 1H), 7.75 (t, 1H), 7.5 (m, 3H), 7.38 (d, 1H), 7.1 (d, 1H), 6.95 (d, 1H), 5.0 (m, 1H), 3.85 (s, 3H), 1.95–1.8 (m, 6H), 1.60 (m, 2H).
EXAMPLE 15
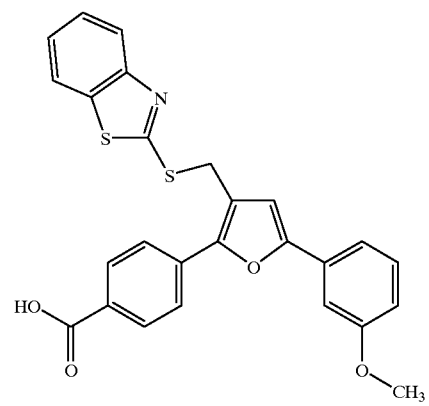
Proton NMR (400 MHz, acetone-d6): 8.16 (d, 2H), 8.02 (d, 2H), 7.92 (d, 1H), 7.82 (d, 1H), 7.50–7.30 (m, 5H), 7.19 (s, 1H), 6.90 (m, 1H), 4.86 (s, 2H), 3.85 (s, 3H).
EXAMPLE 16
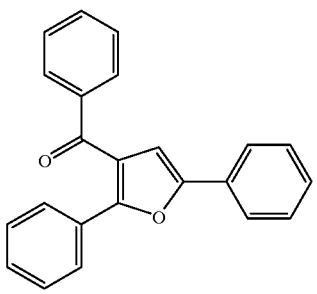
EXAMPLE 17
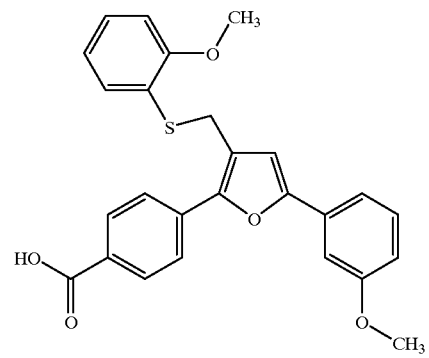
HPLC-MS: 445.3 (M−1).

EXAMPLE 18
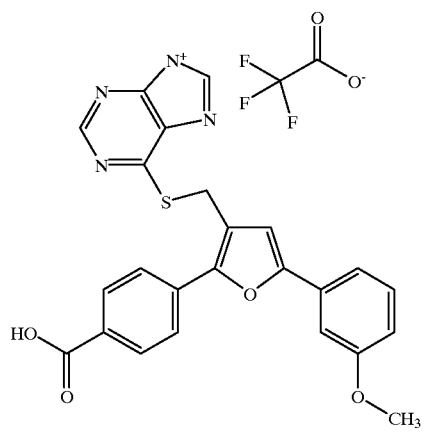
HPLC-MS: 457.1 (M−1).
EXAMPLE 19
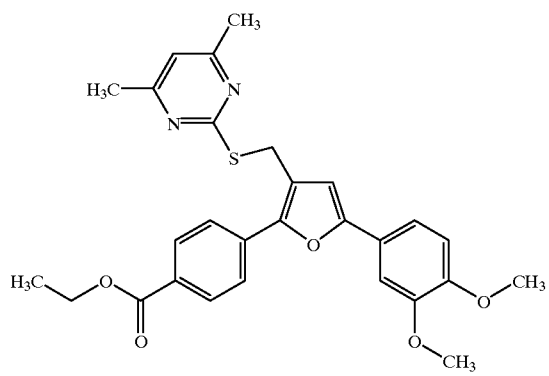
Proton NMR (400 MHz, acetone-d6): 8.20 (d, 2H), 7.94 (d, 2H), 7.38–7.35 (m, 2H), 7.03 (d, 1H), 6.98 (s, 1H), 6.89 (s, 1H), 4.56 (s, 2H), 4.36 (q, 2H), 3.89 (s, 3H), 3.84 (s, 3H), 2.32 (s, 6H), 1.37 (t, 3H).
EXAMPLE 20
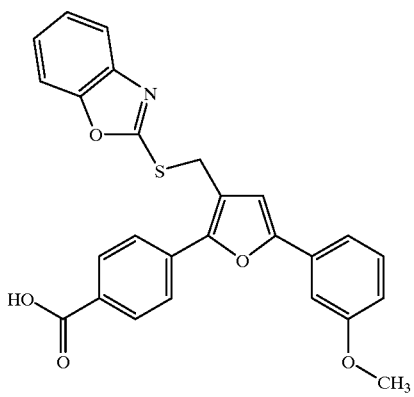
EXAMPLE 21
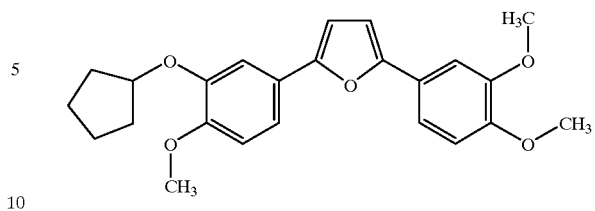
Proton NMR (300 MHz, acetone-d6): 7.3 (dd, 2H), 6.9 (dd, 2H), 7.0 (d, 1H), 6.5 (d, 2H), 4.85 (t, 1H), 4.0 (s, 3H), 3.95 (s, 3H), 1.9–1.6 (m, 8H).
EXAMPLE 22
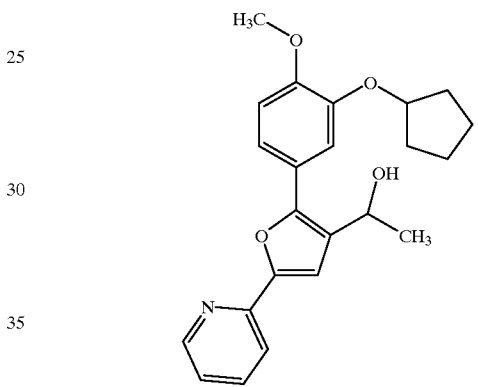
Proton NMR (300 MHz, acetone-d6): 8.55 (d, 1H), 7.82 (m, 2H), 7.47 (s, 1H), 7.36 (d, 1H), 7.28 (s, 1H), 7.21 (d, 1H), 7.12 (m, 1H), 5.05 (m, 1H) 4.9 (m, 1H), 3.85 (s, 3H), 1.95–1.75 (m, 6H), 1.7 (m, 2H) 1.55 (dd, 3H).
EXAMPLE 23
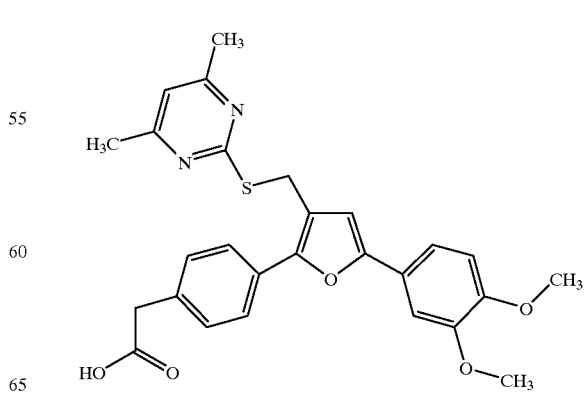

EXAMPLE 24
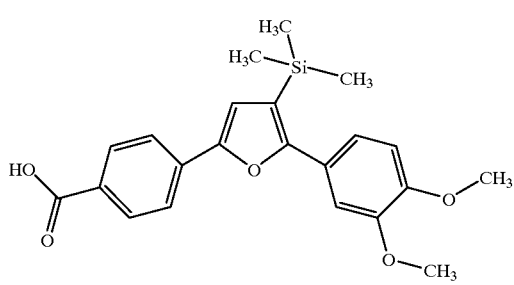
EXAMPLE 25
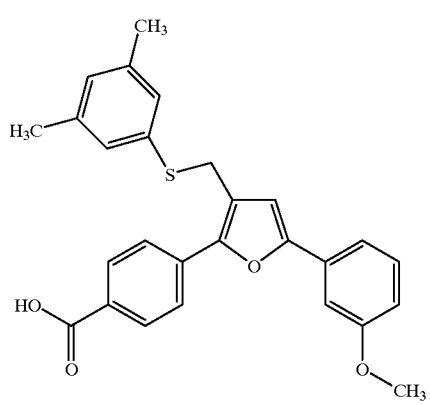
EXAMPLE 26
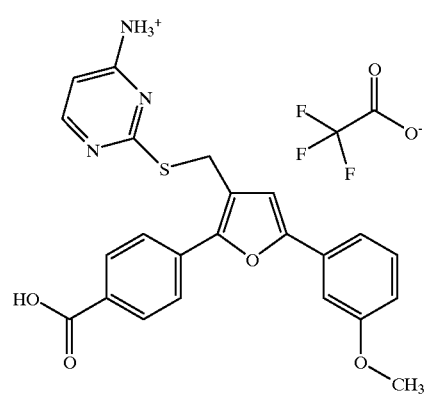
HPLC-MS: 432.3 (M−1).
EXAMPLE 27
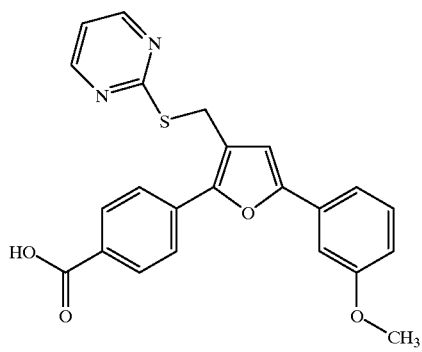
HPLC-MS: 417.2 (M−1).
EXAMPLE 28
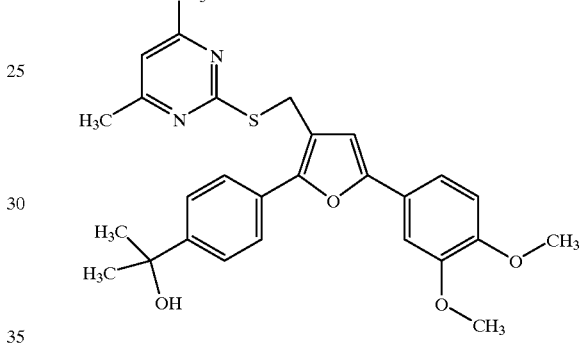
Proton NMR (400 MHz, acetone-d6): 7.77 (d, 2H), 7.64 (d, 2H), 7.35–7.32 (m, 2H), 7.00 (d, 1H), 6.92 (s, 1H), 6.89 (s, 1H), 4.51 (s, 2H), 3.88 (s, 3H), 3.83 (s, 3H), 2.32 (s, 6H), 1.54 (s, 6H).
EXAMPLE 29
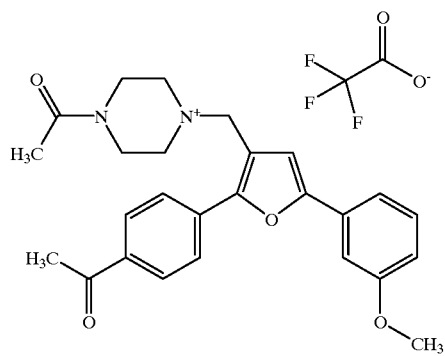
Proton NMR (400 MHz, acetone-d6): 8.13 (d, 2H), 7.96 (d, 2H), 7.46 (s, 1H), 7.39–7.34 (m, 3H), 6.93 (m, 1H), 4.69 (s, 2H), 3.90 (bd, 4H), 3.87 (s, 3H), 3.42 (bd, 4H), 2.08 (s, 3H).

EXAMPLE 30
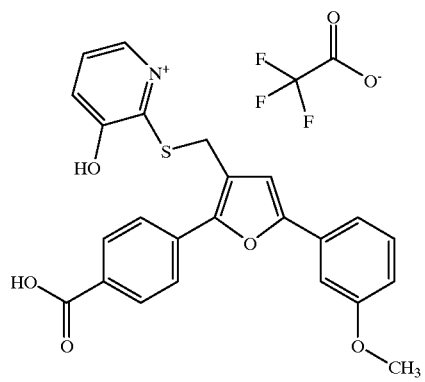
EXAMPLE 31
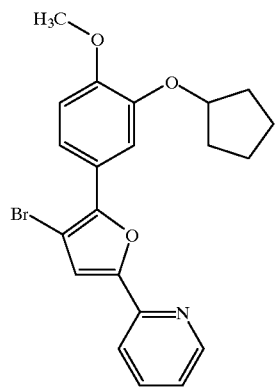
Proton NMR (300 MHz, acetone-d6): 8.50 (d, 1H), 7.85 (m, 2H), 7.43 (m, 2H), 7.23 (m, 2H), 7.05 (dd, 1H), 4.95 (m, 1H), 3.90 (s, 3H), 1.98–1.80 (m, 6H), 1.65 (m, 2H).
EXAMPLE 32
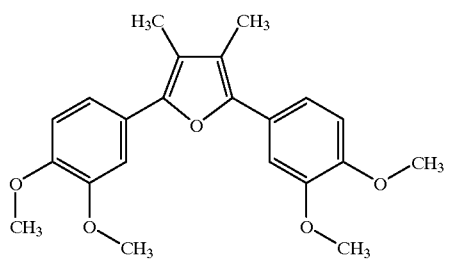
HPLC MS: 309 (M+1)
EXAMPLE 33
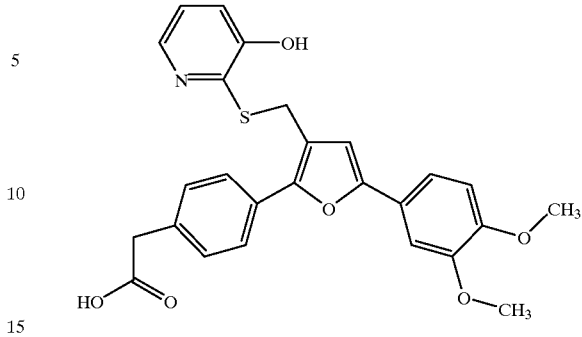
EXAMPLE 34
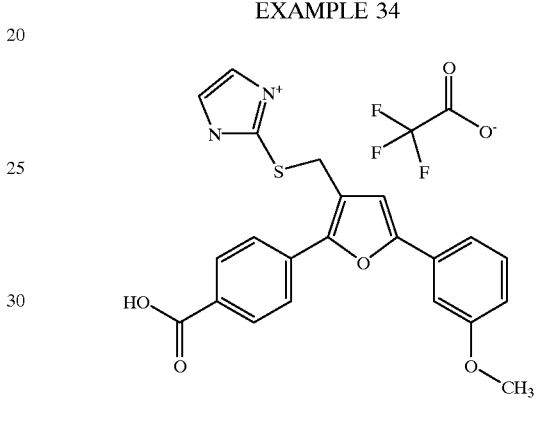
EXAMPLE 35
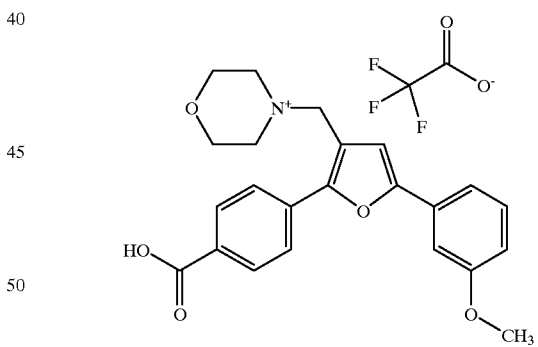
EXAMPLE 36
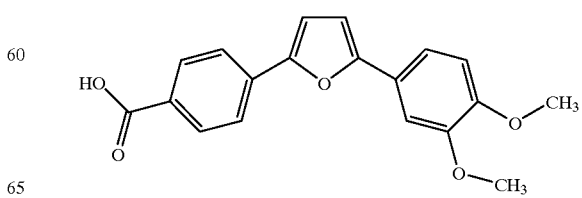

EXAMPLE 37
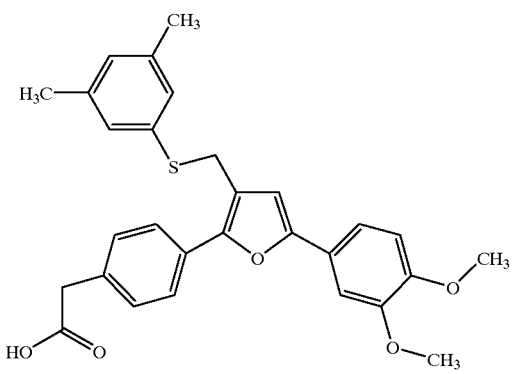
EXAMPLE 38
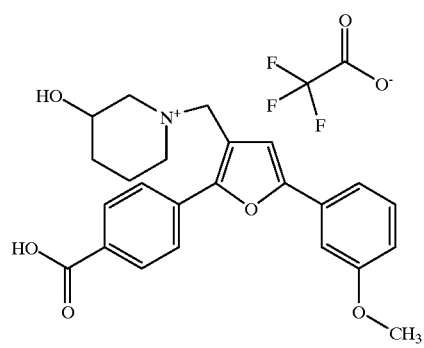
EXAMPLE 39
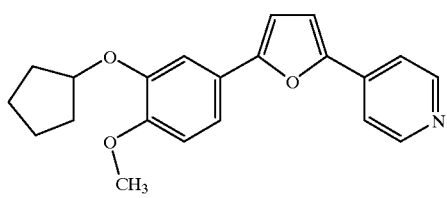
Proton NMR (300 MHz, acetone-d6): 8.54 (d, 2H), 7.68 (d, 2H), 7.42 (dd&s, 2H), 7.25 (d, 1H), 7.05 (d, 1H), 6.9(d, 1H), 4.95 (m, 1H), 3.85 (s, 3H), 2.0–1.8 (m, 6H), 1.62 (m, 2H).
EXAMPLE 40
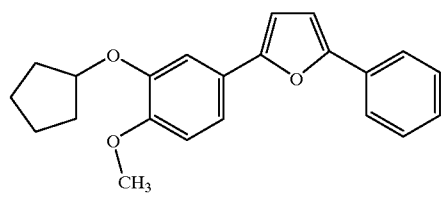
Proton NMR (300 MHz, acetone-d6): 7.75 (s, 1H), 7.4 (t, 2H), 7.28 (m, 4H), 6.90 (d, 1H), 6.72 (d, 1H), 6.58 (d, 1H), 4.95 (m, 1H), 3.9 (s, 3H), 1.98–1.6 (m, 8H).
EXAMPLE 41
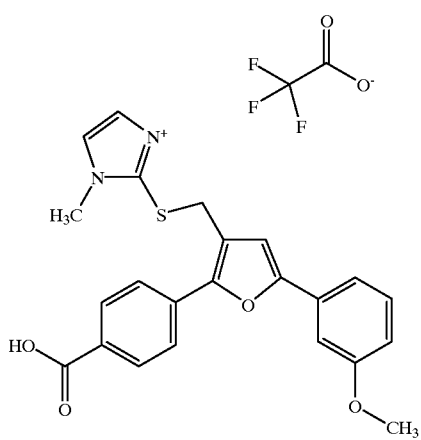
EXAMPLE 42
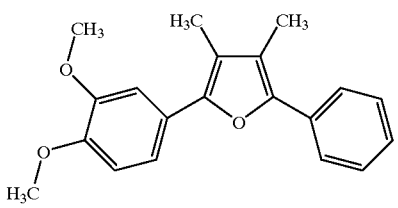
HPLC-MS 369 (M+1)
EXAMPLE 43
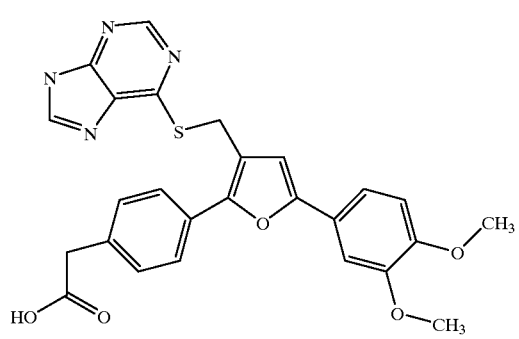
EXAMPLE 44
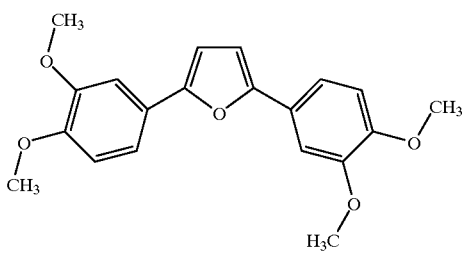

EXAMPLE 45
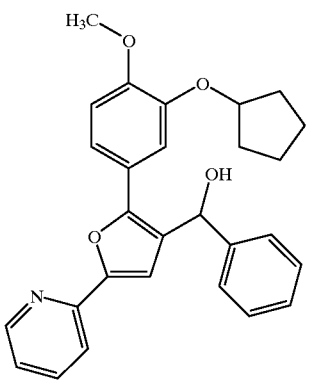
Proton NMR (300 MHz, acetone-d6): 8.5 (d, 1H), 7.8 (bs, 2H), 7.5 (d, 2H), 7.41 (q, 4H), 7.32 (d, 1H), 7.21 (m, 1H), 7.12 (s, 1H), 7.08 (d, 1H), 4.8 (m, 1H), 3.88 (s, 3H), 1.95–1.75 (m, 6H), 1.6 (m, 2H).
EXAMPLE 46
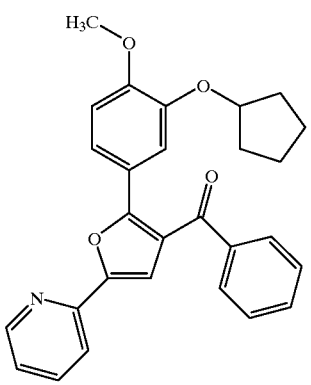
Proton NMR (300 MHz, acetone-d6): 8.58 (d, 2H), 7.92 (m, 4H), 7.63 (d, 1H), 7.53 (m, 3H), 7.41 (d, 1H), 7.32 (bs, 2H), 6.98 (d, 1H), 4.63 (m, 1H), 3.82 (s, 3H), 1.85 (m, 2H), 1.75 (m, 4H) 1.53 (m, 2H).
EXAMPLE 47
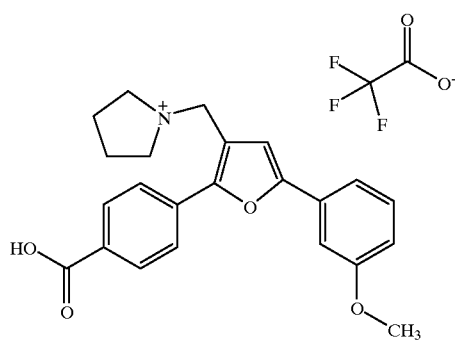
EXAMPLE 48
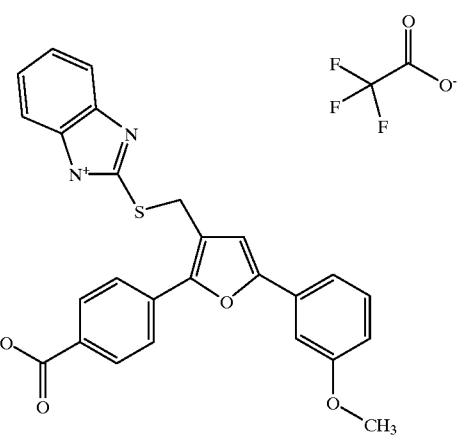
EXAMPLE 49
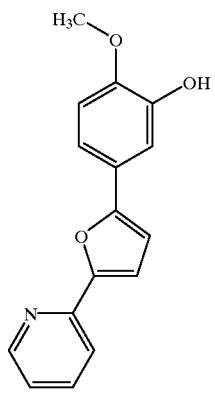
Proton NMR (300 MHz, acetone-d6): 8.55 (d, 1H), 7.85 (s, 1H), 7.80 (dd, 1H), 7.35 (d, 2H), 7.22 (m, 1H), 7.15 (d, 1H), 7.04 (d, 1H), 6.82 (d, 1H), 3.88 (s, 3H).
EXAMPLE 50
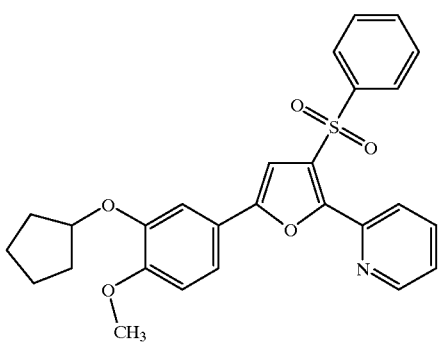
Proton NMR (300 MHz, acetone-d6): 8.68 (d, 1H), 8.18 (d, 2H), 8.05 (bd, 1H), 7.92 (t, 1H), 7.62 (m, 3H), 7.45 (bs, 2H), 7.35 (bs, 2H), 7.08 (d, 1H), 4.98 (m, 1H), 3.84 (s, 3H), 2.0–1.78 (m, 6H), 1.60 (m, 2H).

EXAMPLE 51

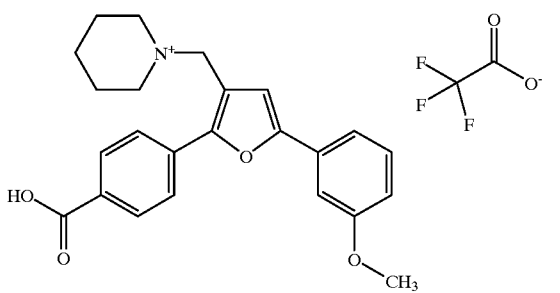

EXAMPLE 52

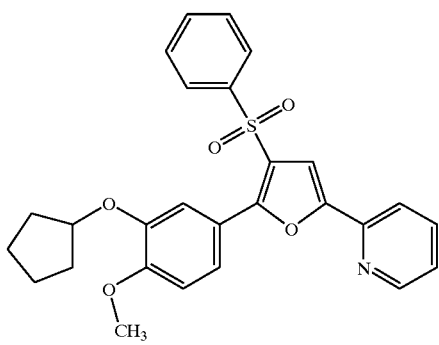

Proton NMR (300 MHz, acetone-d6): 8.61 (d, 1H), 7.91 (m, 4H), 7.61 (m, 5H), 7.43 (s, 1H), 7.35 (m, 1H), 7.08 (d, 1H), 4.91 (m, 1H), 3.9 (s, 3H), 2.0–1.78 (m, 6H), 1.60 (m, 2H).

EXAMPLE 53

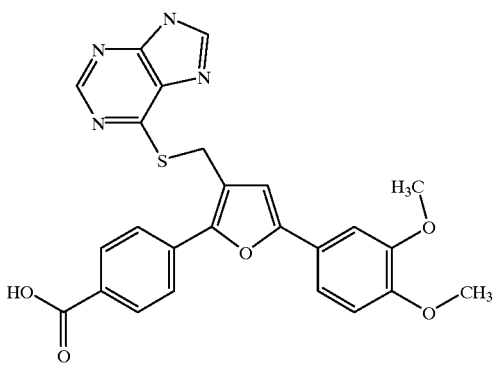

EXAMPLE 54

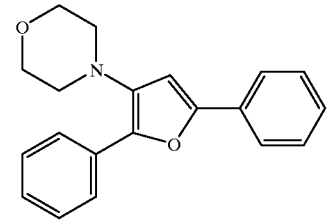

LC-MS 306 (M+1)

Methods of Synthesis

The compounds of the present invention can be prepared by the methods described below. It will be apparent to one skilled in the art that similar methodology could be used to prepare the enantiomers or the racemates of the illustrated compounds.

METHOD A

The 2,5-substituted furans of Formula $I_a$ may be prepared in a multi-step sequence from the requisite aldehyde II. Initial condensation of II with vinyl ketone III in the presence of a suitable base, such as triethylamine, and a suitable catalyst, such as ETB, provides the diketone IV. Treatment of the diketone IV with a suitable acid such as HCl or TsOH, in an inert solvent such as toluene, MeOH or $CH_2Cl_2$ converts to the 2,5-substituted furans of Formula $I_a$

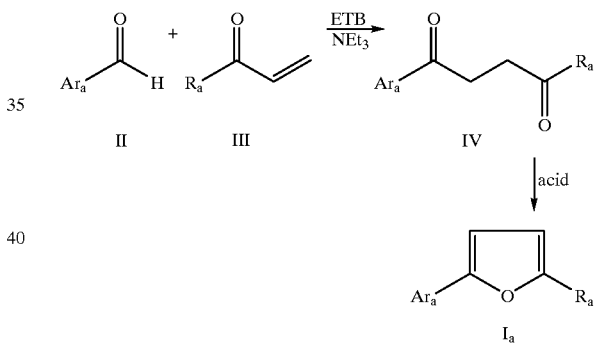

METHOD B

The substituted furans of Formula $I_b$ may be prepared in a multi-step sequence from 2,5-substituted furans of Formula $I_a$. Treatment of $I_a$ with a brominating agent such as NBS with a base such as diisopropylamine or bromine with an acid such as AcOH, provides the brominated furan V. Treatment of the furan V with a suitable base such as BuLi, in an inert solvent such as THF or ether, followed by an electrophile such as an aldehyde afforded VI. Oxidation with an agent such as $MnO_2$ gives compounds of formula 1b

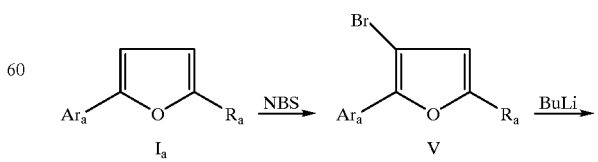

-continued

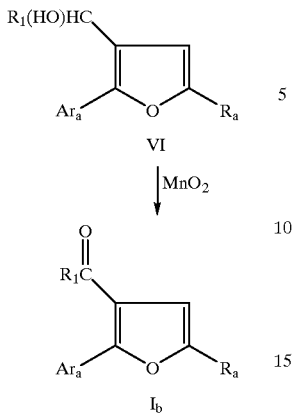

METHOD D

Compounds of general structure $I_e$ in the invention can be constructed according to the solid phase synthetic protocol depicted below. The chemistry involved was similar to that of solution synthesis and is discussed in the experimental section

METHOD C 2,3,5-Tri-substituted furans of general structures $I_c$ and $I_d$ can be constructed by a multi-step scheme in solution according to scheme of method C. A suitable aryl halide (iodide or bromide) of aryl triflate was reacted with zincate 1 under the Negishi coupling reaction conditions (for a review, see: Knochel, P. et al *Chem. Rev.* (1993), 93, 2117) to yield intermediate VII. VII was then reacted with NBS in cold THF and the corresponding dimethyl acetal was hydrolyzed with a suitable acid (or with silica gel) to give aldehyde VIII. Subjection of VIII to the Suzuki cross-coupling reaction with a suitable boronic acid afforded intermediate IX which was reduced to the corresponding alcohol $I_c$. $I_c$ was converted to the bromomethyl compound with dibromotriphenylphosphorane ($Br_2PPh_3$) and the corresponding bromide was then reacted with nucleophiles to furnish $I_d$.

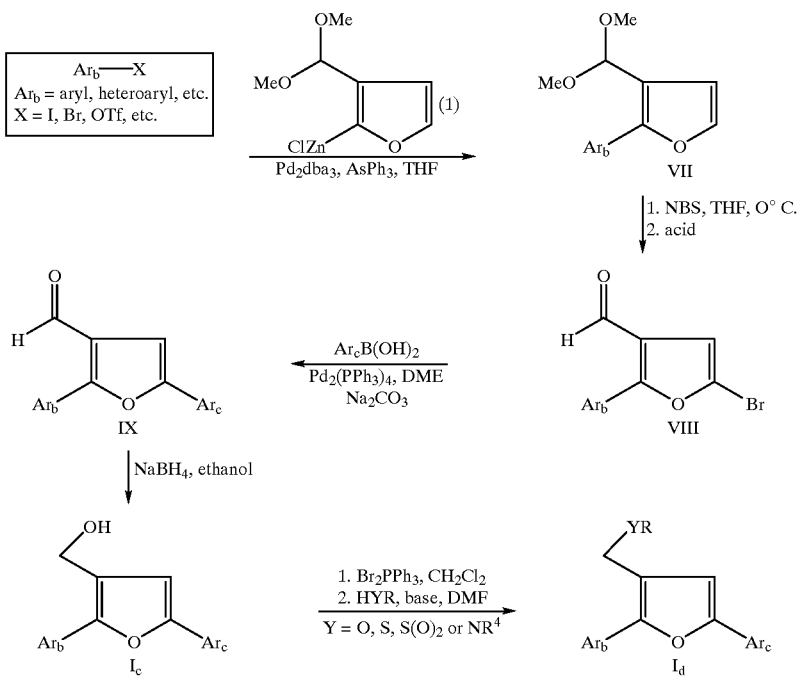

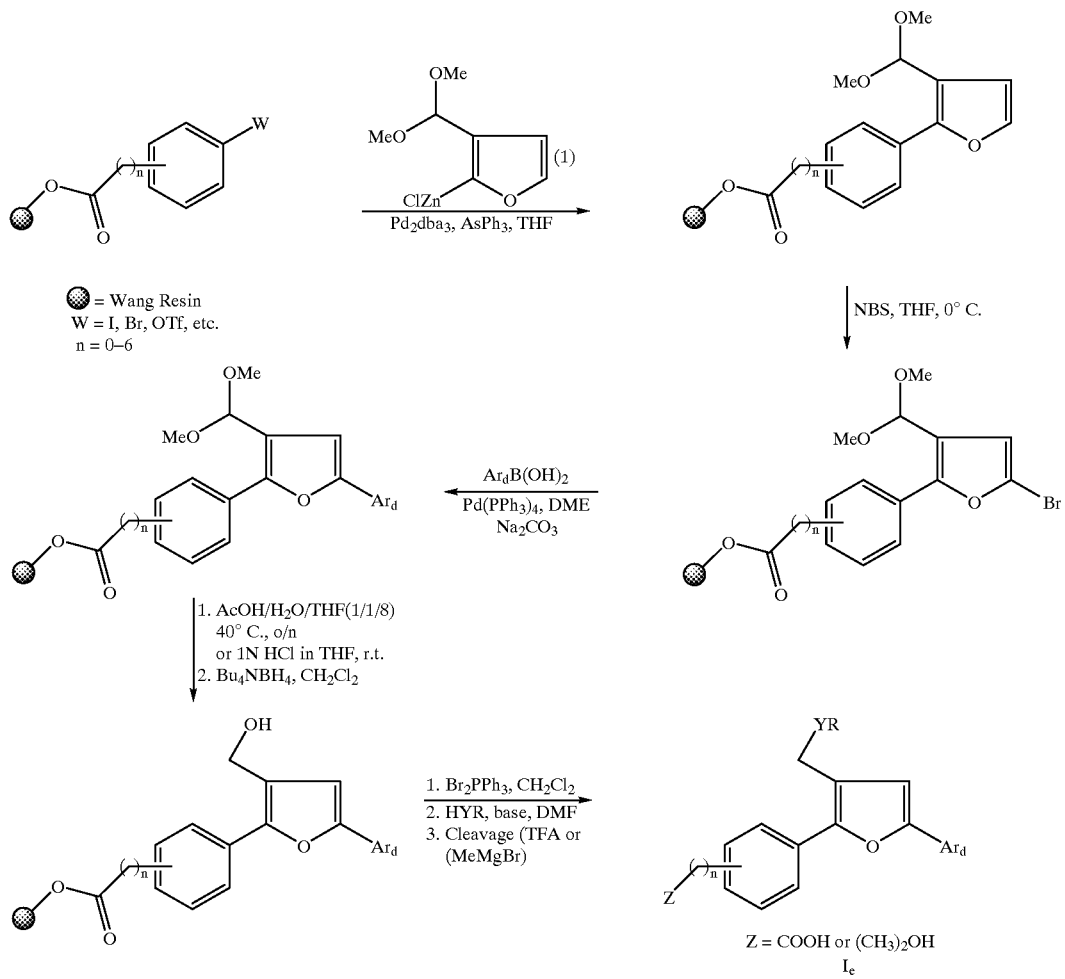

The invention will now be illustrated by the following non-limiting examples in which, unless stated otherwise, all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The example numbers below correspond to the example numbers (1–54) described above. Any examples listed above that are not mentioned or described below can be made by the combination of literature described methods and/or methods disclosed herein.

The following abbreviations have the indicated meanings:
Ac=acetyl
Bn=benzyl
BSA=bovine serum albumin
cAMP=cyclic adenosine-3',5'-monophosphate
DBU=1,8-diazabicyclo[5.4.0]undec-7-ene
DIBAL=diisobutylaluminum hydride
DMAP=4-(dimethylamino)pyridine
DMF=N,N-dimethylformamide
Et$_3$N=triethylamine
ETB=3-ethyl-5-(2-hydroxyethyl)-4-methylthiazolium bromide
GST=glutathione transferase
LDA=lithium diisopropylamide
m-CPBA=metachloroperbenzoic acid
MMPP=monoperoxyphtalic acid
MPPM=monoperoxyphthalic acid, magnesium salt 6H$_2$O Ms=methanesulfonyl=mesyl=SO₂Me
MsO=methanesulfonate=mesylate
NSAID=non-steroidal anti-inflammatory drug
o-Tol=ortho-tolyl
OXONE®=2KHSO₅·KHSO₄·K₂SO₄
PBS=phosphate buffered saline
PCC=pyridinium chlorochromate
PDC=pyridinium dichromate
PDE=phosphodiesterase
Pd₂dba₃=tris(dibenzylideneacetone)dipalladium(O)
Ph=phenyl
Phe=benzenediyl
PMB=para-methoxybenzyl
Pye=pyridinediyl
r.t.=room temperature
rac.=racemic
SAM=aminosulfonyl or sulfonamide or SO₂NH₂
SPA=scintillation proximity assay
TBAF=tetra-n-butylammonium fluoride
Th=2- or 3-thienyl
TFA=trifluoroacetic acid
TFAA=trifluoroacetic acid anhydride
THF=tetrahydrofuran
Thi=thiophenediyl
TLC=thin layer chromatography
TMS-CN=trimethylsilyl cyanide
TNF=tumor necrosis factor
Tz=1H (or 2H)-tetrazol-5-yl
C₃H₅=allyl Alkyl Group Abbreviations
  Me=methyl
  Et=ethyl
  n-Pr=normal propyl
  i-Pr=isopropyl
  n-Bu=normal butyl
  i-Bu=isobutyl
  s-Bu=secondary butyl
  t-Bu=tertiary butyl
  c-Pr=cyclopropyl
  c-Bu=cyclobutyl
  c-Pen=cyclopentyl
  c-Hex=cyclohexyl The following schemes illustrate intermediates to which reference is made in the description of the Examples.

Intermediates and Resins

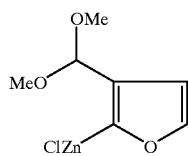

(1)

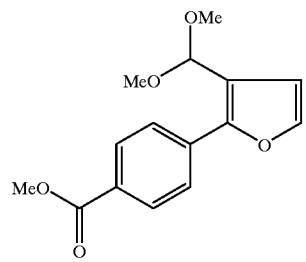

(2)

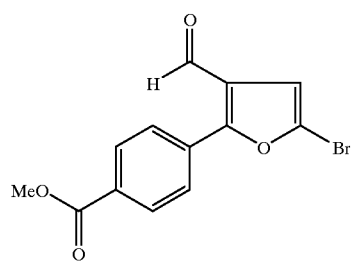

(3)

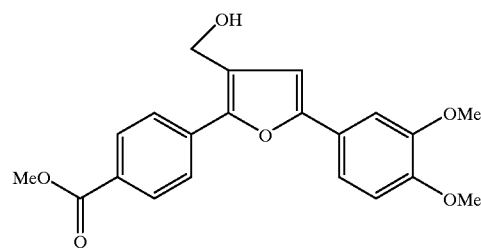

(4)

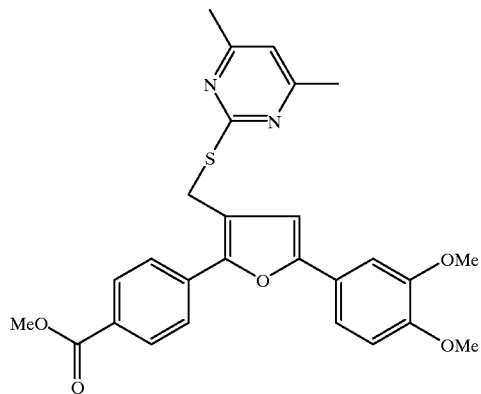

(5)

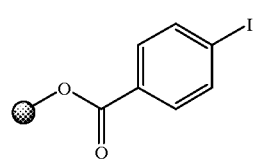

Resin A

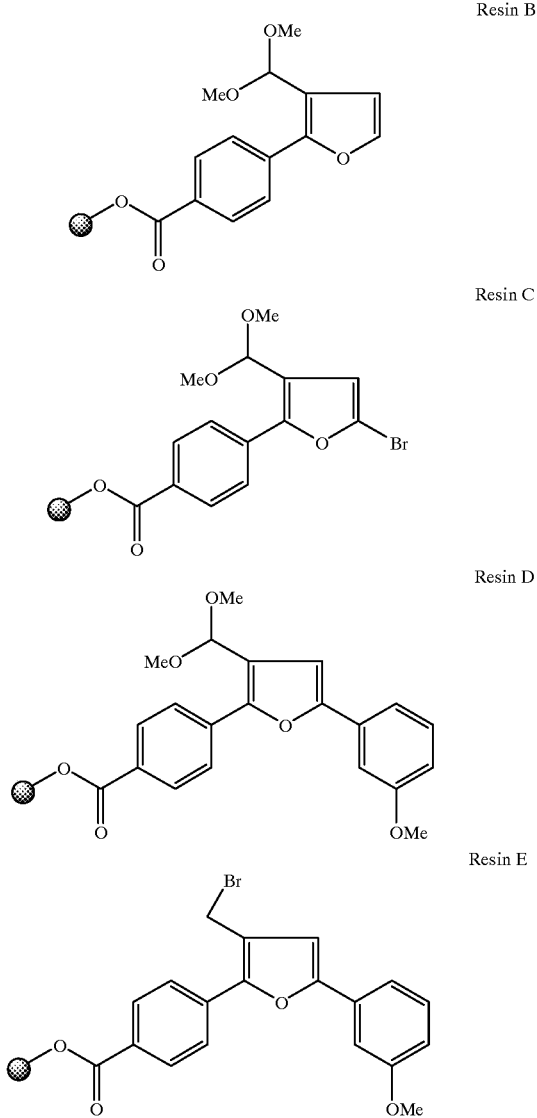

EXPERIMENTAL

Example 1: 2-(3-Cyclobutyloxy-4-methoxyphenyl)-5-(2-pyridyl)furan

Step 1: 1-(3-Cyclobutyloxy-4-methoxyphenyl)-4-(2-pyridyl)-1,4 dione

A mixture of 2-pyridinecarboxaldehyde (9 g), triethyl amine (75 mL) 3-Cyclobutyloxy-4-methoxyphenyl vinyl ketone and ETB were reacted as described in *J. Med. Chem.* 1992, 35, 3474. The title compound was obtained as a white solid in 87% yield.

Step 2: 2-(3-Cyclobutyloxy-4-methoxyphenyl)-5-(2-pyridyl)furan

A mixture of the dione (0.800 g) from Step 1, TsOH (0.410 g) in toluene (3 ml) were stirred at 105° C. for 3 hours. The reaction mixture was quenched with $Na_2HCO_3$, extracted with $CH_2Cl_2$ dried with sodium sulfate and evaporated in vacuo to afford the title compound as a beige solid in 62% yield. $^1$H NMR (300 MHz, acetone-$d_6$): δ 1.7(m, 1H), 1.85 (q, 1H), 2.18 (m, 2H), 2.51 (m, 2H), 3.85 (s, 3H), 4.80 (m, 1H), 6.85 (d, 1H), 7.05 (d, 1H), 7.13 (d, 1H), 7.22 (m, 1H), 7.28 (d, 1H), 7.42 (dd, 2H), 7.85 (dd, 2H), 8.55 (d, 1H).

Examples 2, 3, 4, 14, 21, 39, 40, 44 and 49 were prepared accordingly.

Example 5: 2-(4-carboxyphenyl)-3-(4,6-dimethylpyrimidin-2-yl)-thiomethyl-5-(3-methoxyphenyl)furan Step 1. Preparation of Resin A: To a suspension of Wang resin (10.23 g, Novabiochem, 200–400 mesh, 1.2 mmol/g) in dichloromethane (150 mL) was added 4-iodobenzoyl chloride (6.4 g, 24 mmol), $Et_3N$ (6.7 mL) and DMAP (0.5 g) and the mixture was gently stirred at room temperature overnight. The suspension was filtered and the residual resin was washed sequentially with DMF, DMF/water, dichloromethane and methanol, and dried under reduced pressure to give Resin A (13.15 g).

Step 2. Zincate Coupling: To a solution of 3-dimethoxymethylfuran (1.98 g, 14 mmol) in ether (10 mL) was added n-BuLi (5.6 mL, 2.5M in hexanes) at 0° C. under nitrogen and the mixture was stirred at room temperature for 30 min. $ZnCl_2$ (28 mL, 0.5M in THF) was introduced via a syringe and the resultant solution of Zincate 1 was added to a suspension of Resin 1 (4.15 g) in THF/ether (20 mL, 2:1 v/v) via a cannula at 0° C. under nitrogen. To the mixture was then added a suspension of $Pd_2dba_3$ (77 mg)/$AsPh_3$ (103 mg) in THF (3 mL) and the greenish mixture was allowed to stirred at room temperature gently overnight and then filtered. The resin was washed with THF, THF/$NH_4Cl$ (30% aqueous), water, THF/water, THF, dichloromethane and methanol and then dried under reduced pressure to yield Resin B (4.2 g).

Step 3. Bromination: A suspension of Resin B and NBS (1.48 g) (4.15 g) in THF (40 mL) was stirred at 0° C. for 40 min and filtered. The resin was washed with THF, DMF, THF, dichloromethane and methanol and then dried under reduced pressure to yield Resin C (4.62 g).

Step 4. Suzuki Coupling: To a suspension of Resin C (2 g), 3-methoxyphenyl boronic acid (793 mg, 5.22 mmol) in DME (8 mL) was added $Pd(PPh_3)_4$ (100 mg, 0.087 mmol) and $Na_2CO_3$ (2.2 mL, 2M aqueous) and the mixture was deoxygenated under a stream of nitrogen for 5 min and then heated to reflux for 6 h. After cooling to room temperature, the mixture was filtered and the residual resin was washed with DMF, DMF/water, water, DMF/water, DMF, dichloromethane and methanol and then dried under reduced pressure to afford Resin D.

Step 5. Preparation of Resin E: A suspension of Resin D (2 g) in $H_2O$/AcOH/THF (20 mL, 1:1:8) was shaken on an orbital shaker vigorously at 40° C. overnight and filtered. The resin was washed with THF, dichloromethane and methanol and dried under reduced pressure. The dried resin was then suspended in dichloromethane (29 mL) and $Bu_4NBH_4$ (885 mg) was added and the mixture was again shaken at room temperature overnight and filtered. The residual resin was washed with dichloromethane, DMF, THF and methanol and dried under reduced pressure. To the resin (1.45 g) suspended in dichloromethane (30 mL) was added $Br_2PPh_3$ (1 g) and the mixture was stirred at room temperature for 1 h and filtered. The resin was then washed with dichloromethane, DMF, THF, ethyl acetate and ether and then dried under reduced pressure to yield Resin E.

Step 7. Cleavage with TFA: 200 mg of Resin E was reacted with 5 eq of 4,6-dimethyl-2-mercaptopyrimidine in DMF (2 mL) in the presence of 6 eq of diisopropyl-ethylamine for 1 h and worked up as usual. 80 mg of the dried resin was then cleaved with 20% TFA in dichloromethane (containing 5% dimethyl sulfide) for 20 min and filtered. The resin was washed with dichloromethane (3×) and the filtrate and washing solutions were combined, concentrated and lyophilized to give the title compound as a yellow solid. $^1$H NMR: see Table 1. Cleavage of the same resin with MeMgBr (14 eq) in THF afforded example 6.

Examples 8, 10, 12, 13, 17, 18, 19, 20, 24, 25, 26, 27, 29, 30, 34, 35, 36, 38, 41, 47, 48, 51 and 53 were prepared accordingly.

Example 6: 2-(4-(1-Hydroxy-1-methylethyl) phenyl)-3-(4,6-dimethylpyrimidin-2-yl)thiomethyl-5-(3-methoxyphenyl)furan 200 mg of resin E was reacted as described in step 7 of example 5. Cleavage of the resin with MeMgBr (14 eq) in THF afforded the title compound.

Example 7: 3-Acetoxy-2-(3-cyclopentyloxy-4-methoxyphenyl)-5-(2-pyridyl)furan A mixture of 2-(3-Cyclopentyloxy-4-methoxyphenyl)-5-(2-pyridyl)furan, (50 mg) from example 2, in acetic acid (2 ml) and bromine were stirred for 15 mins. at room temperature. The reaction mixture was quenched with sodium sulfite extracted with EtOAc dried with sodium sulfate and evaporated in vacuo to afford the unexpected title compound as a beige solid in 31% yield. $^1$H NMR (300 MHz, CDCl$_3$): δ 1.6 (m, 2H), 1.98–1.8 (m, 6H), 2.3 (s, 3H), 3.88 (s, 3H), 4.82 (m, 1H), 6.91 (dd, 1H), 7.10 (m, 1H), 7.25 (s, 1H), 7.35 (dd, 2H), 7.7 (bs, 2H), 8.58 (d, 1H).

Example 11: 2-(4-Carboxyphenyl)-5-(3,4-dimethoxypheyl)-3-(4,6-dimethylpyrimidin-2-yl) thiomethylfuran Step 1. Preparation of Zincate 1: To a solution of 3-dimethoxymethylfuran (see: Koenig, H. et al, (1981) *Liebigs Ann. Chem.* 668) (845 mg, 5.95 mmol) in diethyl ether (10 mL) at −78° C. under nitrogen was added n-BuLi (2.4 mL, 2.5M in hexanes) and the mixture was allowed to warm up to room temperature and then heated to reflux for 10 min. ZnCl$_2$ (12 mL, 0.5M in THF) was then introduced via a syringe after the mixture was cooled to room temperature to yield zincate 1.

Step 2. Preparation of Intermediate 2: To the zincate solution under nitrogen at room temperature was added methyl 4-iodobenzoate (770 mg, 2.97 mmol) and a suspension of Pd$_2$dba$_3$/AsPh$_3$ in THF (2 mL). The mixture was then stirred at room temperature for 20 min and then quenched with NH$_4$Cl (saturated aq) and extracted with ether. The extract was washed with water, brine, dried over MgSO$_4$ and filtered. The filtrate was concentrated and purified by flash chromatography (5% ethyl acetate in hexanes+1% Et$_3$N) to yield 2 (750 mg, 92%). $^1$H NMR (400 MHz, CDCl$_3$): δ8.07 (d, 2H), 7.86 (d, 2H), 7.67 (d, 1H), 6.71 (d, 1H), 5.62 (s, 1H), 3.89 (s, 3H), 3.33 (s, 6H).

Step 3. Preparation of Intermediate 3: A mixture of compound 2 (630 mg, 2.28 mmol) and NBS (643 mg) in THF (10 mL) was stirred at 0° C. for 30 min and quenched with 5% aqueous Na$_2$S$_2$O$_3$, and the mixture was worked up as usual. The crude product thus obtained was subjected to flash chromatography (20% ethyl acetate in hexanes) to yield compound 3 (531 mg, 75%) as a white solid after recrystallization from ether/hexanes. $^1$H NMR (400 MHz, acetone-d$_6$): δ10.13 (s, 1H), 8.17 (d, 2H), 8.03 (d, 2H), 7.00 (s, 1H), 3.93 (s, 3H).

Step 4. Preparation of Intermediate 4: To a solution of compound 3 (150 mg, 0.485 mmol) in DME (3 mL) was added 3,4-dimethoxyphenyl boronic acid (97 mg, 0.53 mmol), Pd (PPh$_3$)$_4$ (17 mg) and Na$_2$CO$_3$ (0.27 mL, 2M aq) and the mixture was deoxygenated under a stream of nitrogen for 5 min and heated to reflux for 3 h. The mixture was then cooled to room temperature, diluted with water, extracted with ethyl acetate (3×5 mL). The extracts were combined, washed with water, brine, dried over MgSO$_4$ and filtered. The filtrate was concentrated in uacuo and the residue dissolved in a 1:1 mixture of THF/ethanol. To the solution was added excess NaBH$_4$ and the mixture stirred at room temperature for 10 min, quenched with NH$_4$Cl (aq) and extracted with ethyl acetate (3×10 mL). The extracts were then washed with brine, dried (over MgSO$_4$) and concentrated. The crude product was then purified by flash chromatography (40% ethyl acetate in CH$_2$Cl$_2$) to furnish intermediate 4 (170 mg, 95% yield) as a bright yellow fluorescent solid. $^1$H NMR (300 MHz, acetone-d$_6$): δ8.08 (d, 2H), 7.90 (d, 2H), 7.40 (m, 2H), 7.03 (d, 1H), 6.96 (s, 1H), 4.75 (d, 2H), 4.36 (t, 1H, OH), 3.91 (s, 3H), 3.89 (s, 3H), 3.85 (s, 3H).

Step 5. Intermediate 5: To a solution of 4 (170 mg, 0.46 mmol) in dichloromethane (5 mL) was added Br$_2$PPh$_3$ (234 mg, 0.55 mmol) and the mixture was stirred at room temperature for 30 min. To the mixture was added 4,6-dimethyl-2-mercaptopyrimidine (129 mg) and diisopropylethylamine (0.24 mL) and the solution stirred at room temperature for 1 h, concentrated and the residue was purified by flash chromatography (60% ethyl acetate in hexanes) to afford 5 (190 mg, 84%) as a bright yellow fluorescent solid. $^1$H NMR (300 MHz, acetone-d$_6$/CDCl$_3$): δ8.08 (d, 2H), 7.95 (d, 2H), 7.37–7.35 (m, 2H), 7.00 (d, 1H), 6.96 (s, 1H), 6.87 (s, 1H), 4.55 (s, 2H), 3.89 (s, 3H), 3.88 (s, 3H), 3.84 (s, 3H) 2.32 (s, 6H).

Step 6. Hydrolysis: A mixture of compound 5 (16 mg, 0.032 mmol), LiOH (0.4 mL, 1M solution in water) in dioxane (0.7 mL) was heated to 60° C. for 5 h and cooled to room temperature. The mixture was then acidified with acetic acid and extracted with ethyl acetate. The extract was washed with water, brine, dried over MgSO$_4$, filtered and concentrated to give the title compound as a bright yellow solid. $^1$H NMR: see Table 1.

Example 28: 5-(3,4-Dimethoxyphenyl)-3-(4,6-dimethylpyrimidin-2-yl)thiomethyl-2-[4-(1-hydroxy-1-methylethyl)phenyl]furan To a solution of compound 5 from Example 11 (160 mg, 0.33 mmol) in THF (3 mL) under nitrogen was added MeMgBr (1.2 mL, 1.4M in THF/toluene) and the mixture was stirred at room temperature for 30 min, quenched with NH$_4$Cl and extracted with ethyl acetate. The crude product was purified by flash chromatography (70% ethyl acetate in hexanes) to the title compound as a bright yellow solid (149 mg, 93%). $^1$H NMR: see Table 1.

Example 31: 3-Bromo-2-(3-cyclopentyloxy-4-methoxyphenyl)-5-(2-pyridyl)furan

A mixture of 2-(3-cyclopentyloxy-4-methoxyphenyl)-5-(2-pyridyl)furan, (0.5 g) example 2, in CH$_2$Cl$_2$ (3 ml) and diisopropylamine(21 ul) and NBS (0.320 g) were stirred for 20 mins. at room temperature. The reaction mixture was quenched with Na$_2$CO$_3$, extracted with CH$_2$Cl$_2$ dried with sodium sulfate and evaporated in vacuo to afford the title compound as a beige solid in 63% yield. $^1$H NMR (300 MHz, CDCl$_3$): δ 1.6 (m, 2H), 2.0–1.8 (m, 6H), 3.90 (s, 3H), 4.95 (m, 1H), 7.05 (dd, 1H), 7.23 (m, 2H), 7.43 (m, 2H), 7.85 (dd, 2H), 8.5 (dd, 1H).

Example 45: 3-Alphaphenylmethanol-2-(3-cyclopentyloxy-4-methoxyphenyl)-5-(2-pyridyl) furan To a mixture 3-bromo-2-(3-Cyclopentyloxy-4-methoxyphenyl)-5-(2-pyridyl)furan (from Example 31) in THF (2 ml) at −78° C. was added nBuLi 1.5M (0.2ml). After 5 mins. benzaldehyde (20 ul) was added The reaction mixture was quenched with NH$_4$Cl extracted with EtOAc dried with sodium sulfate and evaporated in vacuo to afford the title compound as a beige solid in 42% yield. $^1$H NMR (300 MHz, CDCl$_3$): δ 1.6 (m, 2H), 1.95–1.8 (m, 6H), 3.88 (s, 3H), 4.8 (m, 1H), 6.0 (s, 1H), 7.12 (s, 1H), 7.08 (d, 1H), 7.21 (m, 1H), 7.32 (d, 1H), 7.41 (q, 4H), 7.5 (d, 2H), 7.8 (bs, 2H), 8.5 (d, 1H).

Examples 22, 50 and 52 were prepared accordingly.

Example 46: 3-Benzoyl-2-(3-cyclopentyloxy-4-methoxyphenyl)-5-(2-pyridyl)furan

A mixture 3-alphaphenylmethanol-2-(3-cyclopentyloxy-4-methoxyphenyl)-5-(2-pyridyl)furan (24 mg, Example 45) in EtOAc (1 ml) and manganese dioxide were stirred for 2 hrs. The reaction mixture was filtered through celite . Flash chromathography (20% EtOAc in hexanes) afford the title compound as a beige solid in 90% yield. $^1$H NMR (300 MHz, CDCl$_3$): δ 1.53 (m, 2H), 1.75 (m, 4H), 1.85 (m, 2H), 3.82 (s, 3H), 4.63 (m, 1H), 6.98 (d, 1H), 7.32 (bs, 1H), 7.32 (bs, 2H), 7.41 (d, 1H), 7.53 (m, 3H), 7.63 (d, 2H), 7.92 (m, 4H), 8.58 (d, 2H).

Examples 9 and 16 were prepared accordingly.

ASSAYS FOR DETERMINING BIOLOGICAL ACTIVITY

Establishment of CHO-K1 Cell Lines Stably Expressing PDE IVa Enzyme

CHO-K1 cells stably expressing the prostacyclin receptor and grown under G418 selection as described previously (Y. Boie, et al, J. Biol. Chem.: 269, 12173–12178, 1994) were plated at a density of 1.75×10$^6$ cells/175 cm$^2$ in a T-175 flask (Gibco, Burlington, Vt.) containing alpha MEM media; 10% heat inactivated fetal bovine serum (FBS); 1% (v/v) penicillin/streptomycin; 25 mM Hepes, pH 7.4; and 500 μg/ml G418 (complete media). The cells were placed in an incubator for 24 hr at 37° C. and 5% CO$_2$. The cells were then washed with warmed sterile phosphate buffered saline (PBS) and incubated with 2 82 g/ml DNA, and 9 μg/ml lipofectamine reagent in Opti-MEM for 7 hr. At 37° C. and 5% CO$_2$. The incubation solution was diluted 1:2 with Opti-MEM containing 20% FBS and incubated overnight. Following the overnight incubation, the media was replaced by complete media containing 500 μg/ml hygromycin B. Colonies were identified and grown in T-175 flasks for further characterization.

Measurement of Whole-cell cAMP Content

CHO-K1 cells were plated at a density of 10$^6$ cells/175 cm$^2$ containing complete media with 500 μg/ml hygromycin. The flasks were maintained in an incubator at 37° C. with 5.0% CO$_2$ for 72 hr. The media was changed and the cells were allowed to grow overnight. The cells were washed and dissociated from the plate with PBS containing 0.5 mM EDTA. Cellular cAMP content was measured by centrifuging the cell suspension at 150 g×10 min. And resuspending the cells in a Hanks buffered salt solution at a density of 0.2×10$^6$ cells/ml. The cells were preincubated at room temperature for 15 min. and then incubated with 10 μM prostaglandin I$_2$ (PGI$_2$) and the indicated compound for an additional 10 min. Basal cAMP levels were determined by incubating the cells in 0.1% DMSO. The incubations were terminated by the addition of HCl (0.1 N final) and the cells measured for cAMP as described below.

Determinations of whole-cell cAMP content were performed by incubating 100 μl reconstituted rabbit anti-succinyl cAMP serum with 100 μl of the whole-cell reaction or known cAMP standard and 30 pmol of $^{125}$I-cAMP TME in a ScintiStrip™ well (300 μl final volume) at room temperature for 18 h. Total cpm (B$_o$) was determined in the absence of sample of cAMP standard. The reaction mixture was then aspirated out of the well, and the individual wells were counted in a Beckman LS 6000 SC with the window open from 10–999 for 1 min. The data were expressed as %B/B$_o$=[(standard or sample cpm−non-specific cpm)/(B$_o$ cpm−non-specific cpm)]×100. Non-specific cpm were determined by incubating only the $^{125}$I-cAMP TME with assay buffer (50 nM acetate; pH 5.8) in the ScintiStrip™ well. All determinations were performed in triplicate.

The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 μM.

Human Whole Blood Assay

Fresh blood was collected in heparinized tubes by venipuncture from healthy volunteers. These subjects had no apparent inflammatory conditions and had not taken any NSAIDs for at least 7 days prior to blood collection. Five hundred μL aliquots of human blood were initially preincubated with either 2 μL DMSO (vehicle) or 2 μL of a test compound at a final concentration of up to 100 μM. Fifteen min later, the blood was incubated with lipopolysaccharide (LPS) at 1 μg/ml (Sigma Chem, #L-2630 from E. coli, serotype 0111:B4; diluted in 0.1% w/v BSA/PBS) for 24 h at 37° C. At the end of the 24 h incubation, the blood was further incubated with an additional amount of LPS (final concentration: 1 μg/ml) for 30 min. This was followed by incubation with f-Met-Leu-Phe (f-MLP) at 1 μM for 15 min. The blood was then centrifuged at 3,300 rpms for 10 min to obtain plasma. The plasma was de-proteinized with methanol and the supernatant was assayed for TNF-α using a commercial ELISA kit (Cistron) and for LTB$_4$ using a EIA kit developed at Merck Frosst.

The instant compounds showed IC$_{50}$ values ranging from 1 nM to 5 μM.

Human Mononuclear Cell Assay

Fresh blood was collected from healthy male volunteers by venipuncture into tubes containing sodium citrate as anticoagulant (10%). The blood was layered on top of histopaque and was centrifuged at 1400 rpm for 35 min at room temperature. After centrifugation, a distinct layer of mononuclear cells (monocytes and lymphocytes) located between the blood and histopaque layers could be aspirated off using a transfer pipette. The mononuclear cells were resuspended in calcium and magnesium free PBS and diluted to 2×10$^6$ cells/ml. One hundred μl aliquots of mononuclear cells were mixed with 2 μl of DMSO (vehicle) or a test compound at a final concentration of up to 10 μM in the presence of 1% or 25% heat-inactivated human serum. Fifteen min. later, the cells were incubated with LPS at a final concentration of 1 μg/ml at 37° C. for 20 h. At the end of the incubation period, the supernatant was obtained by centrifugation at 1000 rpm for 10 min and was assayed for TNF-α using a commercial ELISA kit (Cistron).

The instant compounds showed $IC_{50}$ values ranging from 0.1 nM to 5 μM.

In Vivo Inhibition of Allergen Induced Bronchoconstriction

Guinea pigs, 200 g, are sensitized with a 100 μg/ml ovalbumin in an $Al_2O_3$ suspension in physiological saline. Five hundred μl of this solution are injected intraperitoneally and another 500 μl are injected in 6 ganglionic regions (±75 μl/site). The animals are then housed for 4 to 6 weeks. Thirty minutes prior to the experimentation, the guinea pigs are treated with the test compound or vehicle and with mepyramine maleate, 1 mg/kg. The injection volume is 1 ml/kg of body weight.

After pre-treatment, the animals are placed in a whole body plethysmograph for conscious unrestrained guinea pigs. The animals are challenged for one minute with an aerosol containing ovalbumin in a concentration of 1% in physiological saline. The changes in pulmonary function assessed as changes in enhanced pause or Penh. Penh, a marker of bronchoconstriction, is defined as follows:

Penh=[(expiratory time/relaxation time)−1]*[(peak expiratory flow/peak inspiratory flow]

The results are expressed as the percentage of inhibition of the Penh increase versus the response obtained in a control experiment.

SPA Based PDE Activity Assay Protocol for Measuring Inhibition of Phosphodiesterase Activity Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 ul DMSO), 188 μl of substrate buffer containing [2,8-$^3$H] adenosine 3',5'-cyclic phosphate (cAMP, 100 nM), 10 mM $MgCl_2$, 1 mM EDTA, 50 mM Tris, pH 7.5. The reaction was initiated by the addition of 10 μl of human recombinant PDE-IV isozymes, either expressed and purified from sf9 cells, or from CHO-K1 cells (the amount was controlled so that ~10% product was formed in 10 min. at 30° C.). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. The $IC_{50}$ value was approximated by the non-linear regression fitting of a ten point titration using the standard 4 parameter equation.

$IC_{50}$ values were determined with 100 nM cAMP using the purified GST fusion protein of the human recombinant phosphodiesterase IVa (met-248) produced from a baculovirus/Sf-9 expression system.

What is claimed is:

1. A compound of Formula I

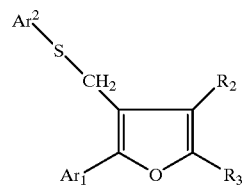

or a pharmaceutically acceptable salt thereof wherein:
  $Ar_1$ is an aromatic ring selected from phenyl, pyridinyl, or furyl, optionally substituted with up to two substituents, each substituent independently is:
   a) $C_{1-6}$alkyl, optionally substituted with —OH, —$CO_2H$, $CO_2C_{1-3}$alkyl, or CN,
   b) $C_{1-6}$alkoxy,
   c) $C_{1-3}$alkylthio,
   d) $C_{1-3}$alkylsulfonyl,
   e) $C_{1-3}$fluoroalkyl, optionally substituted with —OH,
   f) halo,
   g) —OH,
   h) —$CO_2H$, or
   i) —$CO_2C_{1-3}$alkyl;
  $Ar^2$ is an aromatic ring selected from phenyl, benzothiazolyl, benzoxazolyl, pyrimidinyl, pyridinyl, purinyl or imidazolyl, optionally substituted with up to two substituents, each substituent independently is:
   1) $C_{1-6}$alkyl,
   2) $C_{1-6}$alkoxy,
   3) —OH,
   4) halo, or
   5) $CF_3$;
  $R_2$ is
   a) hydrogen or
   b) $C_{1-3}$alkyl; and
  $R_3$ is phenyl, pyridinyl, quinolinyl or furyl, optionally substituted with up to two substituents, each substituent independently is:
   a) $C_{1-3}$alkyl,
   b) $C_{1-3}$fluoroalkyl,
   c) $C_{1-6}$alkoxy,
   d) $C_{1-3}$fluoroalkoxy,
   e) $C_{1-3}$alkylthio,
   f) halo, or
   g) —OH.

2. A compound according to claim 1, wherein $R_2$ is hydrogen and the remaining substituents are defined as in claim 1.

3. A compound according to claim 1, wherein $Ar^2$ is pyrimidinyl, optionally substituted with up to two substituents, each substituent independently is
   1) $C_{1-6}$alkyl,
   2) $C_{1-6}$alkoxy,
   3) —OH, or
   4) halo,
and the remaining substituents are defined as in claim 1.

4. A compound according to claim 1, wherein $Ar_1$ is an aromatic ring selected from phenyl, pyridinyl, or furyl, optionally substituted with up to two substituents, each substituent independently is:
   a) $C_{1-6}$alkyl, optionally substituted with —OH, —$CO_2H$, $CO_2C_{1-3}$alkyl, or CN,
   b) $C_{1-6}$alkoxy, c) $C_{1-3}$alkylthio,
d) $C_{1-3}$alkylsulfonyl,
e) $C_{1-3}$fluoroalkyl, optionally substituted with —OH,
f) halo,
g) —OH,
h) —$CO_2$H, or
i) —$CO_2C_{1-3}$alkyl;
   $Ar^2$ is an aromatic ring selected from phenyl, pyrimidinyl, pyridinyl, purinyl or imidazolyl, optionally substituted with up to two substituents, each substituent independently is:
   1) $C_{1-6}$alkyl,
   2) $C_{1-6}$alkoxy,
   3) —OH, or
   4) halo;
$R_2$ is
   a) hydrogen or
   b) $C_{1-3}$alkyl; and
$R_3$ is phenyl, pyridinyl or quinolinyl, optionally substituted with up to two substituents, each substituent independently is:
   a) $C_{1-3}$alkyl,
   b) $C_{1-3}$fluoroalkyl,
   c) $C_{1-6}$alkoxy,
   d) $C_{1-3}$fluoroalkoxy,
   e) $C_{1-3}$alkylthio,
   f) halo, or
   g) —OH.

5. A compound according to claim 1, wherein said compound is

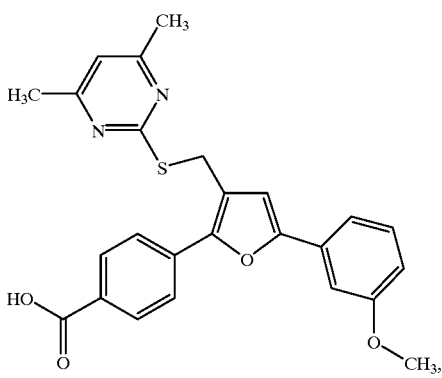

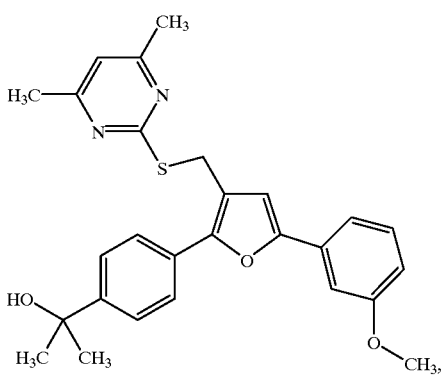

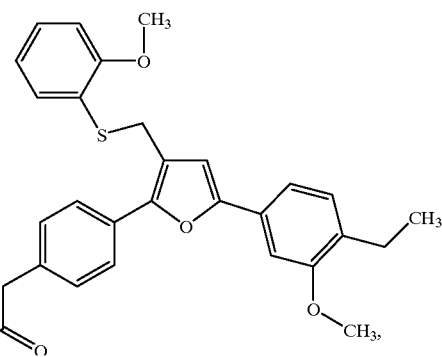

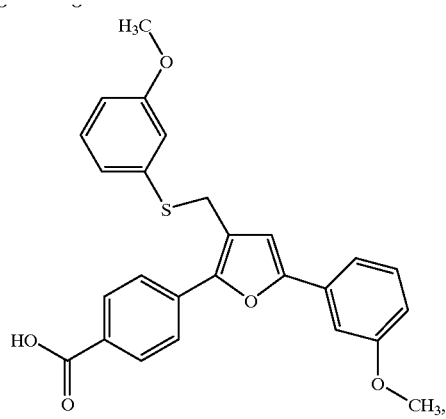

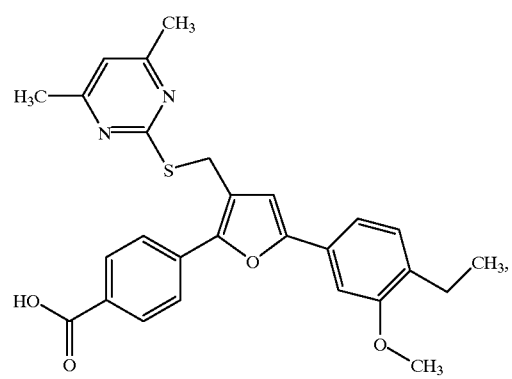

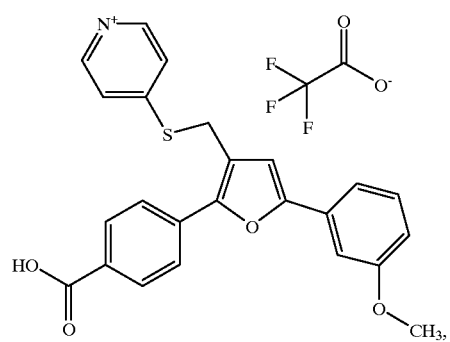

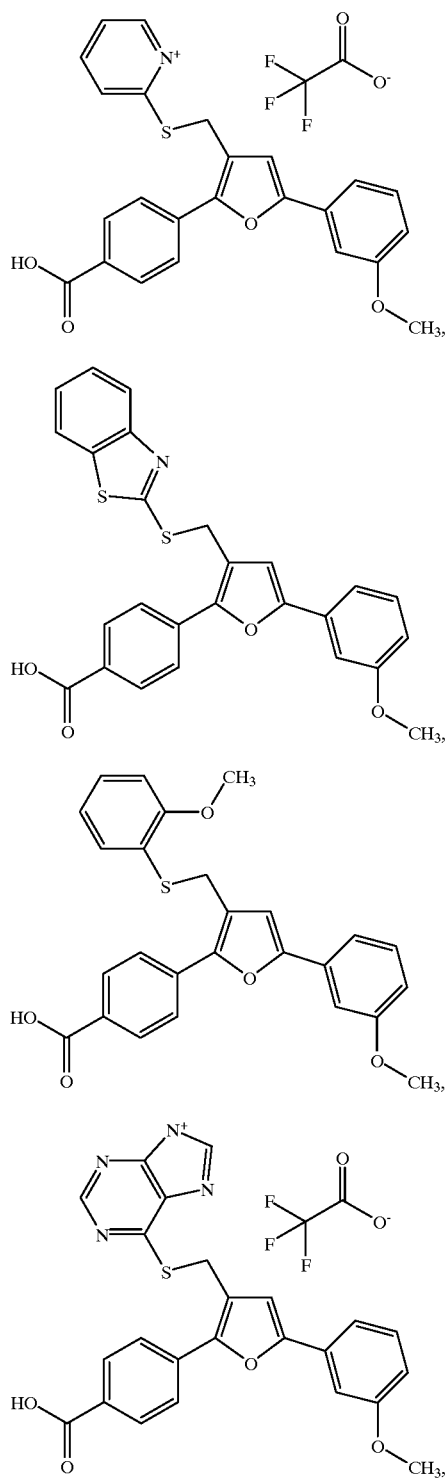
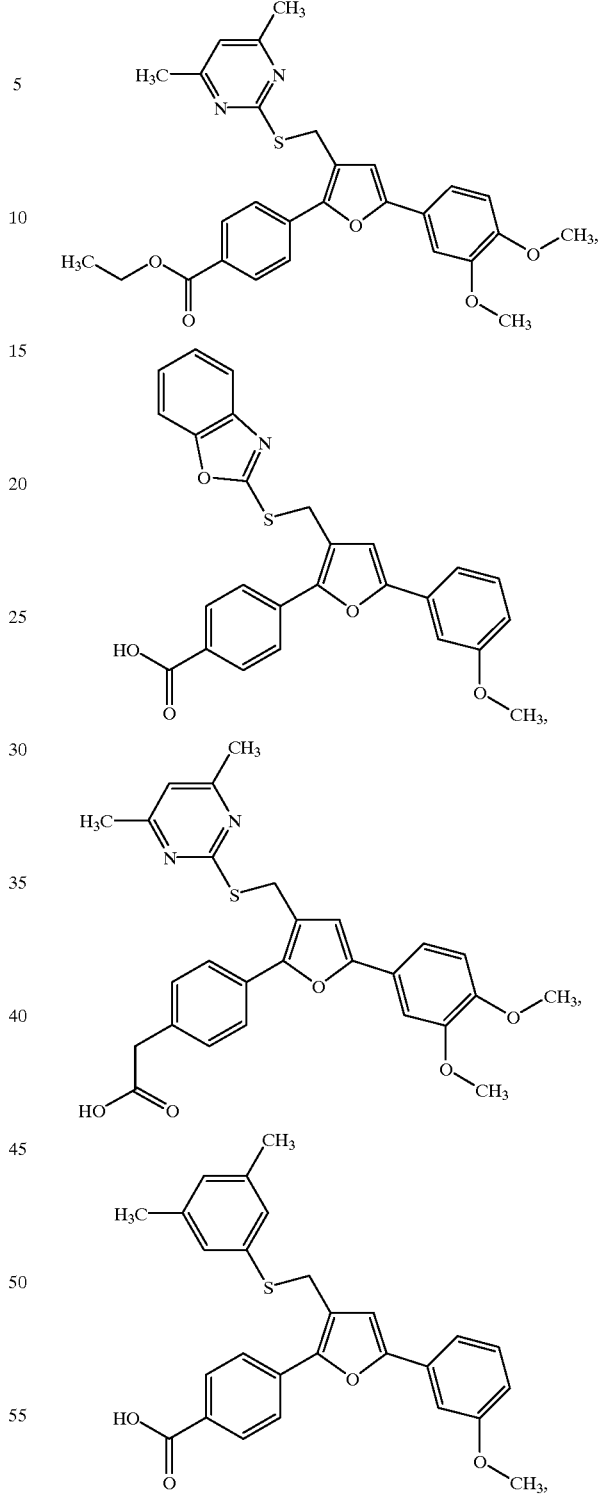

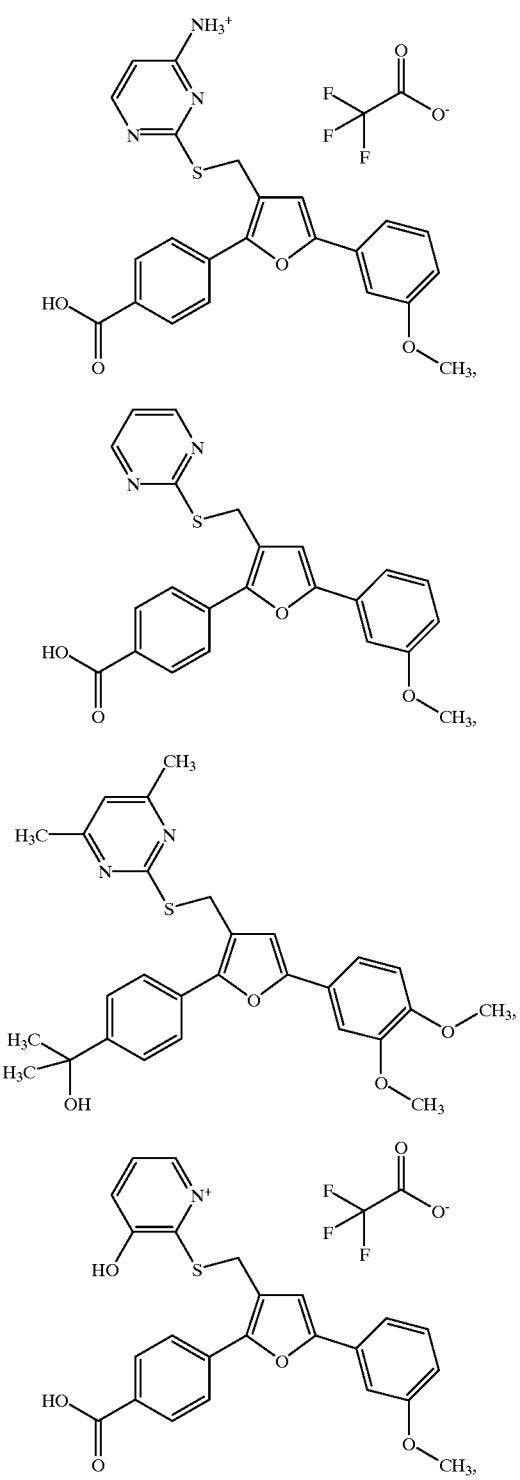
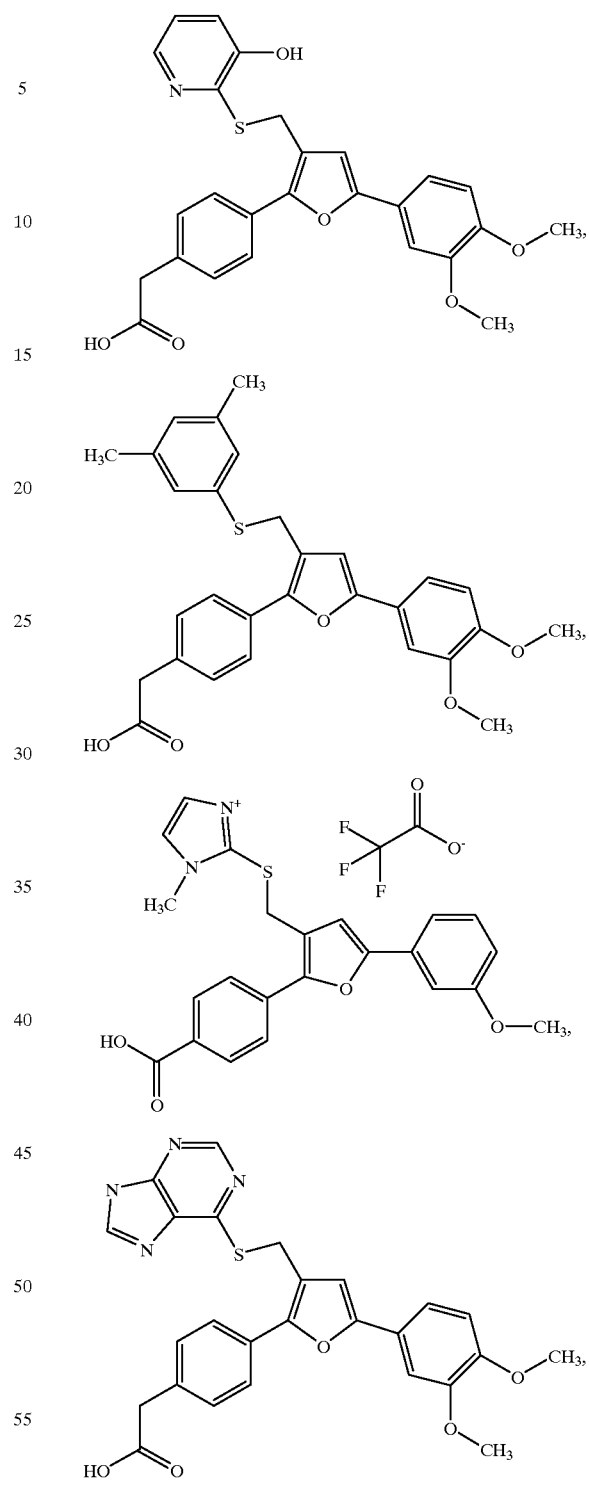

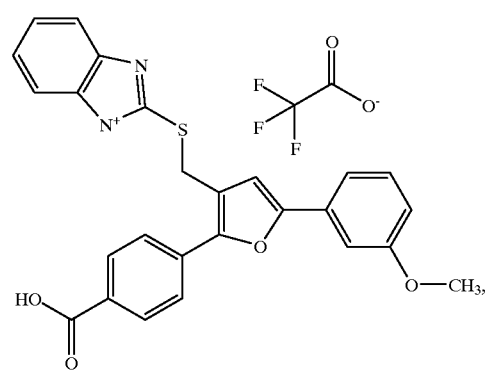

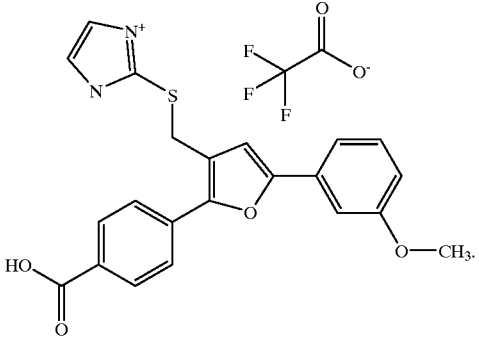

6. A pharmaceutical composition for treating asthma comprising a non-toxic therapeutically effective amount of a compound according to claim 1 and a pharmaceutically acceptable carrier.

7. A pharmaceutical composition for treating disease by increasing the cellular level of cAMP, comprising a non-toxic therapeutically effective amount of a compound according to claim 1 and a pharmaceutically acceptable carrier.

8. A method of treating asthma comprising administration to a patient in need of such treatment of a non-toxic therapeutically effective amount of a compound according to claim 1 and a pharmaceutically acceptable carrier.

9. A method of treating disease by inhibiting PDE IV, said method comprising administration to a patient in need of such treatment of a non-toxic therapeutically effective amount of a compound according to claim 1.

* * * * *